United States Patent [19]
Shiba

[11] Patent Number: 5,483,962
[45] Date of Patent: Jan. 16, 1996

[54] COMPLEX MTI FILTER

[75] Inventor: Akira Shiba, Kawasaki, Japan

[73] Assignee: Fujitsu Limited, Kawasaki, Japan

[21] Appl. No.: 121,642

[22] Filed: Sep. 16, 1993

[30] Foreign Application Priority Data

Mar. 8, 1993 [JP] Japan .................................. 5-046842

[51] Int. Cl.[6] ........................................................ A61B 8/06
[52] U.S. Cl. .................................. 128/660.05; 128/661.09
[58] Field of Search ........................... 128/661.07–661.10;
73/861.25; 342/160–162

[56] References Cited

U.S. PATENT DOCUMENTS

| 4,020,333 | 4/1977 | Nussbaumer | 364/485 |
|---|---|---|---|
| 4,122,448 | 10/1978 | Martin . | |
| 4,137,532 | 1/1979 | Taylor et al. | 342/182 |
| 4,137,533 | 1/1979 | Briechle et al. | 342/160 |
| 4,896,674 | 1/1990 | Seo | 128/661.09 |
| 5,170,792 | 12/1992 | Sturgill et al. | 128/661.09 |
| 5,173,703 | 12/1992 | Mangiapone et al. | 342/159 |
| 5,177,691 | 1/1993 | Welles et al. | 364/485 |
| 5,188,112 | 2/1993 | Sturgill et al. | 128/661.09 |
| 5,246,006 | 9/1993 | Konda et al. | 128/661.09 |
| 5,291,892 | 3/1994 | O'Donnell | 128/661.08 |

Primary Examiner—Francis Jaworski
Attorney, Agent, or Firm—Staas & Halsey

[57] ABSTRACT

Entered complex data is phase-rotated by the corresponding to the moving velocity of the clutter component. Then clutter component information is eliminated by a real type MTI filter assembly. Thereafter, the output data of the real type MTI filter assembly is reversely phase-rotated.

16 Claims, 21 Drawing Sheets

COMPLEX MTI FILTER

BACKGROUND OF THE INVENTION

1. Field of the Invention

The present invention relates to a complex MTI filter, which when obtaining blood flow information within the human body under examination utilizing an ultrasonic Doppler effect, is adapted to separate the blood flow component information from clutter component information.

2. Related Background Art

There has been used an ultrasonic diagnostic system for transmitting ultrasonic beams within the human body and receiving the ultrasounds reflected by a tissue in the human body thus diagnosing diseases of the viscera and the like of the human body. In one aspect of this ultrasonic diagnostic system, or in an optional function of an ultrasonic diagnostic system for displaying a tomographic image (B-mode), there has been used an ultrasonic Doppler diagnostic system in which ultrasounds reflected by blood cells flowing within the human body are received to obtain blood flow information such as velocity, variance, power and the like of the blood flow.

FIG. 12 is a schematic construction view of one example of a conventional ultrasonic diagnostic system.

A transmission control section 11 supplies pulse signals Tp to a number of transducers (not shown) constituting an ultrasonic probe 12 in each specified timing, and thus each transducer transmits ultrasonic pulse beams within the human body under examination (not illustrated). For example, in sector scanning, a specified number (e.g. eight pulses) of ultrasonic pulse beams are emitted along a given direction. The ultrasonic pulse beams are reflected by blood cells flowing within the human body under examination or the other tissues, and are received by each transducer in the ultrasonic probe 12. The received signals Ap received by each transducer are input to a beamformer 13 and is beamformed therein so as to reception dynamic focussing. The received signal S thus obtained is input in a B-mode image detecting section 14 and a blood flow information detecting section 15.

The B-mode image detecting section 14 generates a signal $S_A$ for carrying tomographic image (B-mode) display on the basis of the input received signal S. The signal $S_A$ is supplied to a display section 16 composed of a CRT display or the like, thus displaying a tomographic image for diagnosis.

Meanwhile, the blood flow information detecting section 15 detects blood flow information on the basis of the input received signal S utilizing a Doppler effect as described below.

Namely, the ultrasounds reflected by blood cells within the blood flow are subjected to frequency shift by movement of the blood cells. The frequency shift amount (Doppler shift frequency) $f_d$ is represented by the following equation:

$$f_d = (2V_B \cos \theta / C) \cdot f_c \tag{1}$$

where $V_B$ is the blood flow velocity, $\theta$ is an angle formed by the two intersecting directions of the blood flow and transmitted ultrasonic beam, $f_c$ is a center frequency of the transmitted ultrasounds and C is a velocity of ultrasounds transmitting within the human body.

Further, the center frequency f of the received signal receiving the reflected ultrasounds is represented by as follows:

$$f = f_c + f_d \tag{2}$$

Accordingly, it is possible to detect the blood flow velocity $V_B$ by means of detecting the Doppler shift frequency $f_d$ and in addition detecting a blood vessel extending direction on the basis of the signal $S_A$ for carrying the above tomographic image. The Doppler shift frequency $f_d$ can be obtained using a wide variety of methods, for example, an auto-correlation method, FFT method, and micro-displacement measuring method [a cross-correlation method (Yagi, et al, "Micro-displacement measurement for inhomogeneous tissue utilizing the spatial correlation of analysis signal", pp. 359–360, Literature of No. 54 Meeting of Japan Ultrasonic Medical Institute); a phase tracking method (Araki, et al, "Tissue displacement measurement in living subject by phase tracking processing", pp. 445–446, Literature of No. 57 Meeting of Japan Ultrasonic Medical Institute, and "Ultrasonic Diagnostic System", Japanese Patent Application No. hei 2-273910, Application Date: Oct. 12, 1989); and a method oriented to observation data (Yamagisi, et al, "Estimation method for micro-displacement in a reflected type independently of the random structure of scatterer", pp. 233–234, Literature of No. 56 Meeting of Japan Ultrasonic Medical Institute, and "Ultrasonic Diagnostic System", Japanese Patent Application No. hei 2-088553, Application Date: Apr. 3, 1989)].

The signal $S_B$ carrying blood flow information thus obtained is input in the display section 16 and is, for example, superposed on the above tomographic image, so that the blood flows in the direction of approaching to and separating from the ultrasonic prove are displayed, for example, as red and blue, respectively.

Hereinafter, there will be described only detection of the blood flow information which is the subject matter of the present invention.

FIG. 13 is a block diagram of one example of a portion equivalent to a blood flow information detecting section 15 as shown in FIG. 12 which is involved in the conventional ultrasonic diagnostic system. As shown, the received signal S output from the beamformer is input to a quadrature detector 17 to be detected by 90 degrees.

FIG. 14 is a block diagram showing an internal construction of the quadrature detector 17.

The received signal S input to the quadrature detector 17 is divided into two lines, which are respectively input to multipliers 171 and 172. Meanwhile, the multipliers 171 and 172 receive two sinusoidal signals (carrier signals) cos 2 πvt and −sin 2 πvt, which are different in phase by 90 degrees from each other. The multipliers 171 and 172 multiply the received signal S by the carrier signal: cos 2 πvt, and the received signal S by the=carrier signal: −sin 2 π vt, respectively, thus generating two signals each having both frequencies of addition and difference of the two signals prior to multiplication. These signals are made to pass through low-pass filters 173 and 174, respectively. This generates an I component and Q component of the received signal S after the quadrature detection, each carrying only signal having the frequency of difference between the two signals mentioned above. The I component and Q component of the received signal S, which have been subjected to the quadrature detection, are input into A/D converters 175 and 176 to be A/D converted, respectively, and are then temporarily stored in RAM's (Random Access Memory) 177 and 178.

Thereafter, the I component and Q component of the received signal S after the quadrature detection are read out from the RAM's 177 and 178, and are then input to Moving Target Indicators (MTI) filters 18 and 19 shown in FIG. 13, respectively. The order of read out from the RAM's 177 and 178 is different from the order of load onto the RAM's 177 and 178. For example, the I components and Q components of the eight received signals S on each observation point within the human body under examination, which are obtained when ultrasonic beams are emitted eight times along a given direction within the human body under examination, are read out on each observation point from the RAM's 177 and 178, respectively, in accordance with the order of transmission of the ultrasonic beams.

Now, it is assumed that a certain one point within the human body under examination is selected as a representation point, and signals read out from the RAM's 177 and 178 on the representation point are denoted by $I_i$ (i=0,1, ..., 7), $Q_i$ (i=0,1, ..., 7), respectively.

Each of the MTI filters 18 and 19 to which the signals $I_i$ and $Q_i$ read out from the RAM's 177 and 178, respectively, is a digital filter for cutting off a low frequency signal, similarly to that used in a radar, and is widely used in the field of the ultrasonic Doppler diagnostic system. It is generally composed of a delay circuit providing a delay time equivalent to the repeated cycle of the pulse signals and integral/adding device. The MTI filters 18 and 19 are used to remove clutter component information. In general, the received signal S includes not only blood flow information but also relatively slow clutter component information mixed as high noise. More specifically, the clutter component is owing to the motion of the human body under examination other than the blood flow and consequently has a power 100 times as much as the blood flow component.

The MTI filters 18 and 19 are involved in the subject matter of the present invention, and thus they will be described in detail later. Clutter removed signals $BI_i$ and $BQ_i$ output from the MTI filters 18 and 19, which have excluded the clutter component information, are supplied to an auto-correlator 20. The auto-correlator 20 obtains, on each observation point within the human body under examination, an angle $\Delta\theta$ by an autocorrelation operation on the basis of the equation set forth below:

$$\Delta\theta = \arctan\left\{ \left( \sum_{i=1}^{7} BQ_i \cdot BI_{i-1} - BI_i \cdot BQ_{i-1} \right) / \left( \sum_{i=1}^{7} BI_i \cdot BI_{i-1} + BQ_i \cdot BQ_{i-1} \right) \right\} \quad (3)$$

In this manner, it is possible, on each observation point within the human body under examination, to obtain a blood flow signal $S_B$ carrying the blood flow information such as velocity $V_B$ proportional to the angle $\Delta\theta$, velocity variance $\sigma_B^2$ representative of variation of the angle $\Delta\theta$ and the like of the blood flow.

FIGS. 15(A) and 15(B) are views each showing the characteristic of the MTI filter.

The axis of abscissa represents a Doppler shift frequency $f_d$ (refer to the equation (1)). Further, a polygonal line 31 represents the characteristic of the MTI filter. The MTI filter has such a characteristic so as to cut off the signals within a frequency band of $|f_d| \leq TH$ with $f_d=0$ taken as the center and to pass the signals within a frequency band of $|f_d| > TH$. Further, crests 32 and 33 represent the Doppler shift frequency distributions of the clutter component and the blood flow component carried by the received signal S.

As shown in FIG. 15(A), in a case where the blood flow velocity is high and the crest 33 is greatly separated from the crest 32, the clutter removed signals $BI_i$ and $BQ_i$ (refer to FIG. 13), which have selectively excluded the clutter component information, can be output by means of determining the signal elimination band of the MTI filter to cut off the clutter component information corresponding to the crest 32 and to pass blood flow information corresponding to the crest 33. Meanwhile, in a case where the blood flow velocity is very slow and the crest 33 comes closer to the crest 32, as shown in FIG. 15(B), there will occur such a problem that, by determining the characteristic of the MTI filter to remove the clutter component information, the blood flow component information is also removed, even if the crest 32 is separated from the crest 33 as yet. Accordingly, it is difficult to separately remove only the clutter component information. In particular, there has been enhanced the requirement for detecting the blood flow information of the abdomen portion such as the liver, and therefore, it has become important to detect the very slow blood flow having a Doppler shift frequency similar to that of the clutter components.

FIG. 16 is a block diagram showing a signal processing circuit corresponding to the blood flow information detecting section 15, which is so arranged that even in a case where the Doppler shift frequency of the clutter component comes closer to that of the blood flow component, the clutter component information can be selectively removed; and FIG. 17 is a view showing relationship between characteristic and received signal of the complex filter shown in FIG. 16. In these figures, the elements corresponding to those of FIGS. 13–15 are denoted by the same reference numbers or symbols as those of FIGS. 13–15, and the explanation thereof is omitted.

A complex MTI filter 25 has a disadvantage such that the number of elements constituting the filter is increased thereby enlarging the magnitude of the circuit compared with the common real type MTI filter as shown in FIGS. 13 and 15. On the other hand, it has an advantage such that the center frequency of the signal elimination band is determined into the value other than zero. The signal processing circuit shown in FIG. 16 is made using the above advantage of the complex filter.

An I component $I_i$ and Q component $Q_i$ of the received signal S output from the quadrature detector 17 are input to an auto-correlator 21 to be subjected to auto-correlation, without removing the clutter component information, thereby obtaining a moving velocity $V_c$ of the clutter component and its variance $\sigma_c^2$ on each observation point within the human body under examination. In this case, the signals input in the auto-correlator 21 include both the clutter component and blood flow component information. However, since the clutter component has a power 100 times (40 dB) as much as the blood flow component, there can be obtained, without any problems, the moving velocity $V_c$ of the clutter component and its variance $\sigma_c^2$ by performing the auto-correlation operation for the signal including the blood flow component information. The signal representative of the moving velocity $V_c$ of the clutter component and its variance $\sigma_c^2$ thus obtained is input to a memory 22. The memory 22 previously stores, as the type of look-up table, a corresponding table of the moving velocity $V_c$ to a factor for determining the center frequency $f_0$ of the signal elimination band in the complex MTI filter 25, and a corresponding table of the variance $\sigma_c^2$ to a factor for determining the band width W of the signal elimination band in the complex MTI filter 25. The memory 22 receives the moving velocity $V_c$ and its variance $\sigma_c^2$ obtained in the auto-correlator 21 and outputs the factor for determining the center frequency $f_0$ the band width W of the signal elimination band in the complex MTI filter 25 to the complex MTI filter 25.

Further, the I component $I_i$ and Q component $Q_i$ of the received signal S output from the quadrature detector 17 are also supplied to delay circuits 23 and 24, respectively, so as to provide the delay for a time required for obtaining the moving velocity $V_c$ and its variance $\sigma_c^2$ in the auto-correlator 21 and for passing the factors obtained in the memory 20 on the basis of the obtained moving velocity $V_c$ and its variance $\sigma_c^2$ to the complex MTI filter 25, and are then applied to the complex MTI filter 25. The complex MTI filter 25 has the characteristic determined by the above factors so as to selectively only clutter components (crest 32) as shown in FIG. 17. Accordingly, the blood flow component (crest 33) can be effectively taken out.

Incidentally, the variance $\sigma_c^2$ of the moving velocity $V_c$ of the clutter components is easily obtained experimentally or experientially. Accordingly, the band width W of the signal elimination band in complex MTI filter 25 is fixed at the value previously determined experimentally or experientially, and only the moving velocity $V_c$ of the clutter components is obtained in the auto-correlator 21, thus determining the center frequency $f_0$ of the signal elimination band in complex-MTI filter 25. Incidentally, the fixed band width W may be preferably changed according to the measured positions of the human body under examination.

In some determinations of the center frequency $f_0$ and band width W of the signal elimination band in the complex MTI filter 25, the direct current component ($f_d=0$) may be out of the signal elimination band. However, there may be input into the complex MTI filter 25 the signal having the unnecessary direct current component caused by offsets of multipliers 171 and 172 as shown in FIG. 12 constituting the quadrature detector 17 and amplifier (not shown). Accordingly, the signal elimination band may preferably include $f_d=0$ so as to cut-off the direct current component of the signal input to the complex MTI filter 25.

As described above, the complex MTI filter permits the center frequency $f_0$ of the signal elimination band to be determined at one other than $f_0=0$. Consequently, for example, the signal processing as shown in FIG. 16 makes it possible to effectively take out the blood flow information selectively removing the clutter component information, even in a case where the Doppler shift frequency of the clutter component comes closer to that of the blood flow component, as far as they do not overlap each other. However, if the conventional MTI filters are simply combined to form the complex MTI filter, such arrangement will enlarge the circuit scale, and thus it is not practical.

Hereinafter, first, the conventional common real type MTI filter will be explained, and then the complex MTI filter constituted by simply combining the real type MTI filters will be explained.

FIG. 18 is a circuit block diagram of a moving average type (MA type; Finite Inpulse Response (FIR) type) MTI filter, as an example of the conventional real type MTI filter shown in FIG. 13.

The moving average type MTI filters 18 and 19 comprise multipliers $181_{13}$ 0, 181__0 ..., 181__7; 191__0, 191__1, .., 191__7 for multiplying input signals $I_i$ and $Q_i$ by factors K0, K1, ..., K7, delay circuits 182__0, 182__1, ..., 182__6; 192__0, 192__1, ..., 192__6 for delaying the signals subjected to the above multiplication, and adders 183__0, 183__1, ..., 183__6; 193__0, 193__1, ..., 193__6 for performing addition of tile delayed signals and output signals of the associated multipliers, respectively.

The conventional typical ultrasonic diagnostic system uses a four-order (four pieces of multipliers for multiplying input signal by factors are used) moving average type of MTI filter. However, nowaday clinic requires to detect also the blood flow in such a low velocity that it is close to the moving velocity of the clutter component. In order to satisfy this requirement, there is a need to provide a fine filter characteristic, and it is preferable to use an eight-order moving average type of MTI filter as shown in FIG. 18.

If the moving average type of MTI filter as shown in FIG. 18 is used and then the factors K0, K1, ..., K7 are suitably selected, as seen in FIGS. 15(A) and (B) it is possible to eliminate the signals within a frequency band of $|f_d| \leq TH$ centering $f_d=0$ where $f_d$ denotes a Doppler shift frequency.

FIG. 19 is a circuit block diagram of an autoregressive type (AR type; Infinite Inpulse Response (IIR) type) MTI filter, as another example of the conventional real type MTI filter.

The autoregressive type MTI filter does not need a large scale of circuit in extent of the moving average type MTI filter. However, according to this type of filter, the response is varied in accordance with initial values of the input signals $I_i$ and $Q_i$. Consequently, the autoregressive type MTI filter is not adapted, in comparison with the the moving average type MTI filter, for use ].n such an ultrasonic diagnostic system that only, for example, eight data are provided on each observation point within the human body under examination. Incidentally, it is noted that the present invention is not involved in the type of the real type MTI filter.

FIG. 20 is a circuit block diagram of a complex MTI filter comprising the real type of moving average type MTI filter.

Assuming that two input signals I and Q are expressed by a complex number I+jQ consisting of a real part and an imaginary part (j denotes imaginary number unit); a complex factor $K_R+jK_I$; and a result obtained through a multiplication of the complex number I+jQ by the complex factor $K_R+jK_I$ is denoted by BI+ jBQ, the following equation is given:

$$BI + jBQ = (I + jQ) \cdot (K_R + jK_I) = \qquad (4)$$
$$(I \cdot K_R - Q \cdot K_I) + j(Q \cdot K_R + I \cdot K_I)$$

The complex filter shown in FIG. 20 is arranged with the real type MTI filter patterned after the equation (4).

The complex MTI filter shown in FIG. 20 is over twice as large as the circuit scale of the real type MTI filter shown in FIG. 18. According to such a complex MTI filter, in order to selectively remove the clutter component information, it is necessary to interchange 16 pieces of factors $K_{R0}, K_{R1}, \ldots, K_{R7}; K_{I0}, K_{I1}, \ldots, K_{I7}$ on each observation point of the human body under examination in synchronism with the moving velocity and the like of the clutter component on the observation point. The implementation of this requirement needs a large scale of table and thus needs a large storage capacity of memory 22 as shown in FIG. 16, for example, many Read Only Memories (ROM). Consequently, the circuit scale will be extremely enlarged in its entirety, and it is not of practical use from the point of view of the setting space and the manufacturing cost of the equipments.

FIG. 21 is a circuit block diagram of a complex MTI filter comprising the real type of autoregressive type MTI filter as shown in FIG. 19.

The complex MTI filter shown in FIG. 21 is also over twice as large as the circuit scale of the real type MTI filter shown in FIG. 19.

Regarding a technology of obtaining the blood flow information upon separating it from the clutter component information, U.S. Pat. No. 5,170,792 discloses another example of the prior art. According to the scheme disclosed in U.S. Pat. No. 5,170,792, a signal output from a Doppler system processor system, which corresponds to the quadrature detector 17 shown in FIG. 13 of the present application, is phase-rotated by the corresponding velocity of the clutter component, and the signal subjected to the phase rotation is input to a MTI filter so that the clutter component information is eliminated. According to this scheme, there will be observed a blood flow velocity relative to the clutter component, which is obtained by means of subtracting a clutter component velocity to the ultrasonic probe 12 from a blood flow velocity to the ultrasonic probe 12. This is a useful scheme in such a requirement that a blood flow within internal organs is observed cancelling movement or performance of the internal organ itself, but it is not a general-purpose scheme. For instance, as in case of the heart, in a case where the clutter and the blood move independently of each other, it would be difficult to observe a proper blood flow velocity with respect to the heart of interest.

Further, the scheme disclosed in U.S. Pat. No. 5,170,792 has been associated with an additional big problem which will occur when the apparatus is assembled.

Specifically, in the quadrature detector 17 shown in FIG. 13 of the present application and the corresponding Doppler system processor system referenced to in U.S. Pat. No. 5,170,792, a DC offset emanates. It will be a cause of the superposition of the DC component on signals. Further, there is a possibility of the superposition of the DC component on signals due to various causes such as the ultrasonic component reflected by a stationary object. In order to obtain an exact blood flow velocity, however, it is necessary to completely remove those DC components. According to U.S. Pat. No. 5,170,792, a stationary bias signal canceller is used to remove the DC components. However, the stationary bias signal canceller is placed at upper stream stage than the tissue velocity estimation/compensation and the MTI filter with respect to a signal flow. Thus, there is a possibility such that the DC component is superposed on an input signal of the velocity estimator for obtaining the blood flow velocity owing to the bit error (occurrence of error caused by the fact that the numbers less than the Least Significant Digit can not be given) in the digital arithmetic operation in the mid course on the path in which a signal output from the stationary bias signal canceller reaches the velocity estimator for obtaining the blood flow velocity, and owing to the transient response in the MTI filter and the like. In this case, it would be difficult to detect a blood flow signal in a critical point with respect to the noise level and thus the apparatus would be limited in accuracy of the detection. Incidentally, according to the scheme of U.S. Pat. No. 5,170,792, the stationary bias signal canceller is permitted only to be placed at upper stream stage than the tissue velocity estimation/ compensation with respect to a signal flow, and is not permitted to be placed immediately before the velocity estimator for obtaining the blood flow velocity.

SUMMARY OF THE INVENTION

In view of the foregoing, it is therefore an object of the present invention to provide a complex MTI filter having a simple structure and capable of being implemented with the low cost in manufacturing.

It is another object of the present invention to provide a complex MTI filter, when which is applied to an ultrasonic diagnostic system, capable of obtaining an absoute blood flow velocity to an ultrasonic probe, but not a relative blood flow velocity to a clutter component velocity.

It is still another object of the present invention to provide a complex MTI filter, when which is applied to an ultrasonic diagnostic system, permitting a DC elimination filter to be placed lower stream stage than the complex MTI filter with respect to a signal flow.

FIG. 1 is a block diagram showing the principle of the complex MTI filter according to the present invention. Now it is assumed that eight complex data representing the complex number $I_i+jQ_i$ (i=0, 1, ..., 7), which are involved in each observation point of the human body under examination, are sequentially applied to the complex MTI filter. Further, eight angle data representing the angle $\theta_i$ (i=0, 1, ..., 7) are also sequentially applied to the complex MTI filter.

The complex MTI filter according to the present invention basically comprises first phase rotating means 1, first and second real type MTI filters 2 and 3, and second phase rotating means 4. The first phase rotating means 1 receives angle data and complex data, which are associated with each other, and rotates a phase of a complex number $I_i+jQ_i$ represented by the received complex data by an angle $\theta_i$ indicated by the associated angle data.

The first phase rotating means 1 may be provided with complex multiplication means for performing a complex multiplication of a complex number represented by the complex data entered said first phase rotating means 1 by an additional complex number consisting of the real part and the imaginary part which are given by cosine and sine of an angle represented by the angle data entered said first phase rotating means, respectively.

The first and second real type MTI filters 2 and 3 receive data representative of the real part and the imaginary part of the complex number, which have been subjected to the phase rotation by said first phase rotating means 1. These real type MTI filters are not restricted in the type. That is, each may be a filter of any of moving average type, autoregressive type and autoregressive moving average type which is a combination of the moving average type and the autoregressive type. Further, it is preferable that the real type MTI filters 2 and 3 include factor selecting means for selecting filter factors of said first and second real type MTI filters 2 and 3, respectively. The real type MTI filters 2 and 3 provide predetermined filtering processes for the data representative of the real part and the imaginary part of the complex number, respectively, in accordance with the filter factors.

The second phase rotating means 4 receives angle data and complex data of which real part and imaginary part are given with said data subjected to the predetermined filtering processes by said first and second real type MTI filters 2 and 3, respectively, which angle data and complex data are associated with each other. The second phase rotating means 4 rotate a phase of a complex number represented by the received complex data by an angle which is the same as the angle $\theta_i$ indicated by the associated angle data in the absolute value but is of inverse sign. Similar to the first phase rotating means 1, the second phase rotating means 4 may also be provided with complex multiplication means for performing a complex multiplication of a complex number represented by the complex data entered said second phase rotating means 4 by an additional complex number consisting of the real part and the imaginary part which are given by cosine and sine of an angle represented by the angle data entered said second phase rotating means, respectively.

FIG. 2 is a block diagram showing the principle of a modification of the complex MTI filter according to the present invention. According to the complex MTI filter according to the present invention as shown in FIG. 2, in addition to the elements shown in FIG. 1, there are provided angle accumulating means 5 for receiving angle data to sequentially accumulate angles $\Delta\theta$ itself indicated by the received angle data so as to obtain accumulated angles, and cosine and sine calculating means 6 for obtaining data representative of cos $\theta_i$ and sin $\theta_i$ of the accumulated angles $\theta_i$ obtained by said angle accumulating means and supplying the thus obtained data in the form of angle data to the first and second phase rotating means 1 and 4.

The cosine and sine calculating means 6 may be so arranged to obtain cos $\theta_i$ and sine $\theta_i$ based on the accumulated angles $\theta_i$ through the calculation. Alternatively, it may be provided with the type of look-up table in which the angles $\theta_i$ serves as address and cos $\theta_i$ and sine $\theta_i$ serve as contents.

In this manner, according to the present invention, instead of every entry of the rotating angle $\theta_i$ for the complex number $I_i+jQ_i$ from the exterior, it may be so arranged, as shown in FIG. 2, that the received angles $\Delta\theta$ itself are sequentially accumulated to obtain the accumulated angles (rotating angle) $\theta_i$.

Further, the cosine and sine calculating means 6 may be provided, as shown in FIG. 2, independently of the first and second phase rotating means 1 and 4. Alternatively, it may be so arranged to be incorporated into the first and second phase rotating means 1 and 4.

FIG. 3 is a block diagram showing the principle of another modification of the complex MTI filter according to the present invention. According to the complex MTI filter according to the present invention as shown in FIG. 3, there are provided, at the last stage of the complex MTI filter, direct current (DC) elimination filters 7 and 8. There is a possibility that signals output from the quadrature detector 17 (refer to FIG. 13) are superposed on the offset voltage. In a case where this offset voltage is involved in problems, it is preferable to provide the DC elimination filters 7 and 8 as shown in FIG. 3.

The complex MTI filter according to the present invention is effective specifically to extract a fluid (e.g. blood flow) information within the human body under examination utilizing a ultrasonic Doppler effect. In this case, applied to the first phase rotating means 1 and the second phase rotating means 4 is angle data being indicative of an angle corresponding to the movement of the clutter within the human body under examination, which movement being measured by utilizing an ultrasonic Doppler effect.

FIGS. 4–6 are views useful for understanding an operational principle of the complex MTI filter according to the present invention in conjunction with an ultrasonic Doppler effect. It is not certainly that coordinates depicted in FIGS. 4–6 correspond to each other between the respective drawings. Hereinafter, the explanation will be made referring to the arrangement shown in FIG. 2.

It is assumed that data after quadrature detection, on a certain point within the human body under examination, to which ultrasonic pulse beams are emitted eight times to obtain data, is given by $(I_i, Q_i)$ (i=0, 1, . . . , 7). When the ultrasonic pulse beams are emitted eight times, if the clutter component on the observation point within the human body under examination moves at a predetermined velocity, the phase of the received ultrasonic signal will be shifted by the corresponding to the movement of the clutter component. Thus, as shown in FIG. 4, points on complex coordinates of eight pieces of data $(I_i, Q_i)$ are each depicted at the location rotated by the angle $\Delta\theta_i$ (i=0, 1, . . . , 7) which is substantially proportional to a moving velocity $V_c$ of the clutter component.

Hence, the average value $\Delta\theta$ of the angle $\Delta\theta_i$ (i=0, 1, . . . , 7) is obtained in accordance with the following equation:

$$\Delta\theta = \arctan \left\{ \left( \sum_{i=1}^{7} Q_i \cdot I_{i-1} - I_i \cdot Q_{i-1} \right) / \left( \sum_{i=1}^{7} I_i \cdot I_{i-1} + Q_i \cdot Q_{i-1} \right) \right\} \quad (5)$$

The thus obtained average value $\Delta\theta$ is applied to the angle accumulating means 5. The angle accumulating means 5 obtains an accumulating angle $\theta_i=n\Delta\theta$ (n denotes integer sequentially counted up one by one; n=0, 1, . . . , 7) on the basis of the input angle $\Delta\theta$ (average value).

The cosine and sine calculating means 6 obtains cos $\theta_i$ and sin $\theta_i$ on the basis of the accumulating angle $\theta_i$ output from the angle accumulating means 5. The data representative of cos $\theta_i$ and sin $\theta_i$ of the accumulated angles $\theta_i$ are passed to the first and second phase rotating means 1 and 4.

The first phase rotating means 1 is operative to rotate the respective data $(I_i, Q_i)$ (i=0, 1, . . . , 7) sequentially entered by the angle $\theta_i=n\Delta\theta$ in such a direction that they are superposed on a specified data $(I_0 Q_0)$, that is, clockwise, in case of FIG. 2, so that the respective data $(I_i, Q_i)$ come closer to the position of the data $(I_0 Q_0)$. More specifically, performed is a complex multiplication of a complex number represented by the respective data $(I_i, Q_i)$ by an additional complex number consisting of the real part and the imaginary part which are given by cosine and sine of the angle $\theta_i=n\Delta\zeta$, respectively. In this manner, as shown in group A of FIG. 5, such a complex multiplication causes eight data to come closer to each other.

To change the view point, this indicates that in FIG. 15, the clutter component information 32 shifts on the axis of the Doppler shift frequency $f_d$ to a position centering $f_d=0$. The thus frequency-shifted data are supplied to the first and second real type MTI filters 2 and 3. These real type MTI filters 2 and 3 are, as shown in FIG. 15, to eliminate the signals within a frequency band of $|f_d| \leq TH$ centering $f_d=0$ where $f_d$ denotes a Doppler shift frequency. Specifically, as stated above, since the clutter component information 32 shifts on the axis of the Doppler shift frequency $f_d$ to a position centering $f_d=0$, the use of the real type MTI filters makes it possible to effectively eliminate the clutter component.

The data passed through the first and second real type MTI filters 2 and 3 are involved in components due to the blood flow excluding components due to the clutter. This indicates that the group A shown in FIG. 5 shifts to a group B. Data of the group B are involved in data wherein blood flow information is extracted, and as exemplarily shown in the group B the phase is rotated on each data. This phase rotating amount corresponds to the blood flow velocity. However, the data of the group B include influence of the frequency shift due to the phase rotation in the first phase rotating means 1 as well as the blood flow information. Thus, it is necessary to perform the frequency shift by the same amount in the opposite direction.

Hence, the output data of the first and second real type MTI filters 2 and 3 are passed to the second phase rotating means 4. The second phase rotating means 4 is operative to rotate the respective data by the angle, which is the same as the angle $\theta_i=n\Delta\theta$ in the first phase rotating means 1, in a direction opposite to the rotating direction in the first phase rotating means 1, that is, counterclockwise, in this case. As a result, the data as shown in FIG. 6 are obtained. An average value $\Delta\psi$ of angles $\Delta\psi_i$ shown in FIG. 6 is given by the following equation:

$$\Delta \psi = \arctan \left\{ \left( \sum_{i=1}^{7} Q_i \cdot I_{i-1} - I_i \cdot Q_{i-1} \right) / \right.$$
$$\left. \left( \sum_{i=1}^{7} I_i \cdot I_{i-1} + Q_i \cdot Q_{i-1} \right) \right\} \quad (6)$$

The average value $\Delta \psi$ is proportional to the blood velocity $V_B$.

In this way, provision of the respective phase rotating means before and after the two real type MTI filters makes it possible to implement a complex MTI filter in its entirety. And in addition, as will be described later in the preferred embodiments, the phase rotating means can be realized with an extremely smaller scale circuit comparing with the real type MTI filter, and thus iris possible to extremely reduce the circuit scale of the equipment comparing with the conventional complex MTI filter provided with twice real type MTI filters. Further, according to the complex MTI filter of the present invention, it is sufficient to prepare the filter factors by half of that of the conventional complex MTI filter, and thus it is possible to save a ROM for storing the filter factors and the associated wirings, thereby reducing the circuit scale and contributing to the lower cost.

While the above description was made with regard to the principle of the complex MTI filter shown in FIG. 2, there may be considered various modifications. For example, instead of the provision of the angle accumulating means 5, it may be arranged such that the rotating angle $\theta_i$ for the complex number $_i$+j$Q_i$ is calculated in the exterior, and data representative of the rotating angle $\theta_i$ are applied to the complex MTI filter. Further, in FIG. 2, the cosine and sine calculating means 6 is shown such that it is independently of the first and second phase rotating means 1 and 4. However, it is acceptable to arrange the complex MTI filter in such a manner that the equivalence of the operation to be carried out by the cosine and sine calculating means 6 is performed in the interior of the first and second phase rotating means 1 and 4, individually. Furthermore, for example, as shown in FIG. 3, taking into consideration of the combination with the quadrature detector 17 (refer to FIG. 16), it may be arranged such that the complex MTI filter is provided with DC elimination filters 7 and 8.

The objects and features of the present invention will become more apparent from the consideration of the following detailed description taken in conjunction with the accompanying drawings.

DESCRIPTION OF THE PREFERRED EMBODIMENTS

Preferred embodiments of the present invention will be described in detail with reference to the accompanying drawings.

Figure 7:
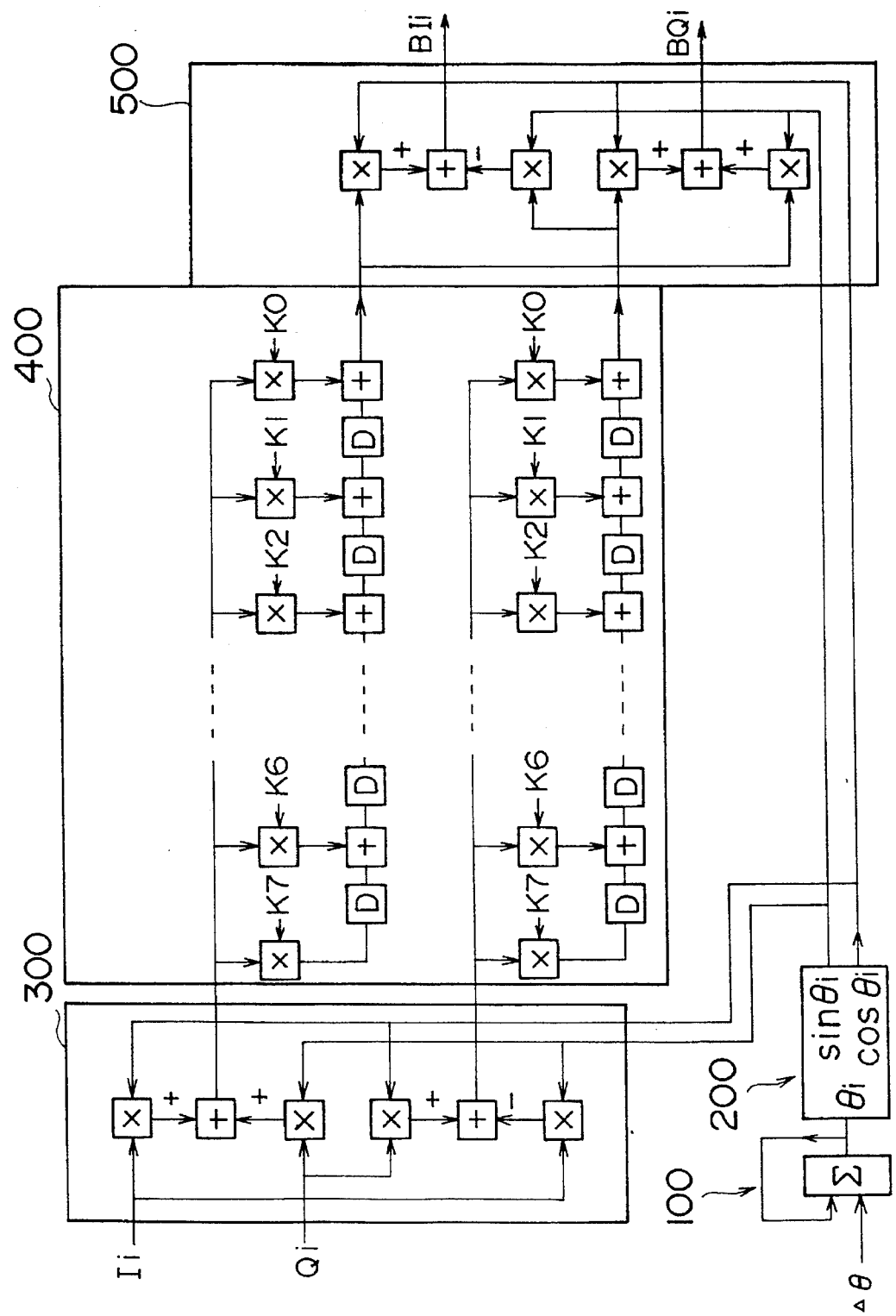
FIG. 7 is a circuit diagram of the complex MTI filter according to the first embodiment of the present invention.

FIG. 7 is a circuit diagram of the complex MTI filter according to the first embodiment of the present invention.

Figure 1:
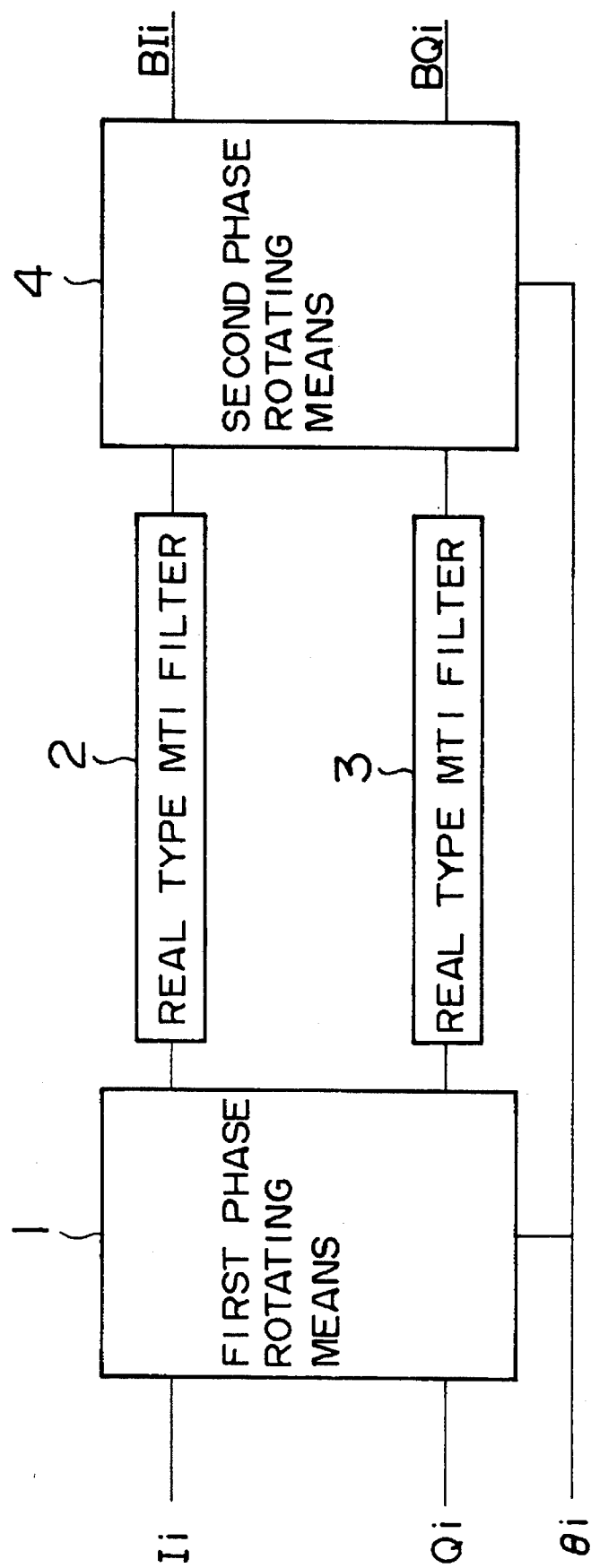
FIG. 1 is a block diagram showing the principle of the complex MTI filter according to the present invention.
Figure 2:
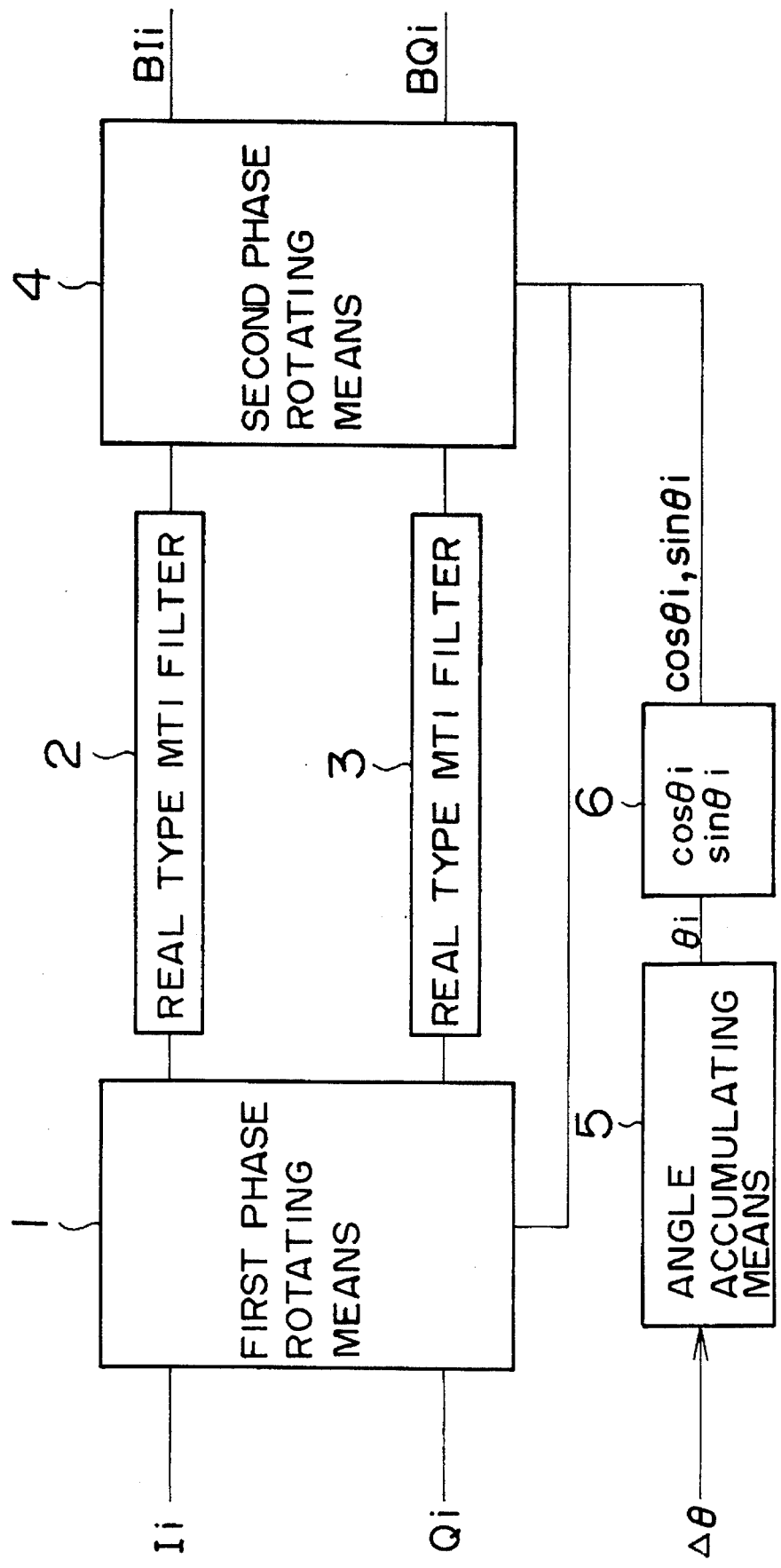
FIG. 2 is a block diagram showing the principle of a modification of the complex MTI filter according to the present invention.
Figure 3:
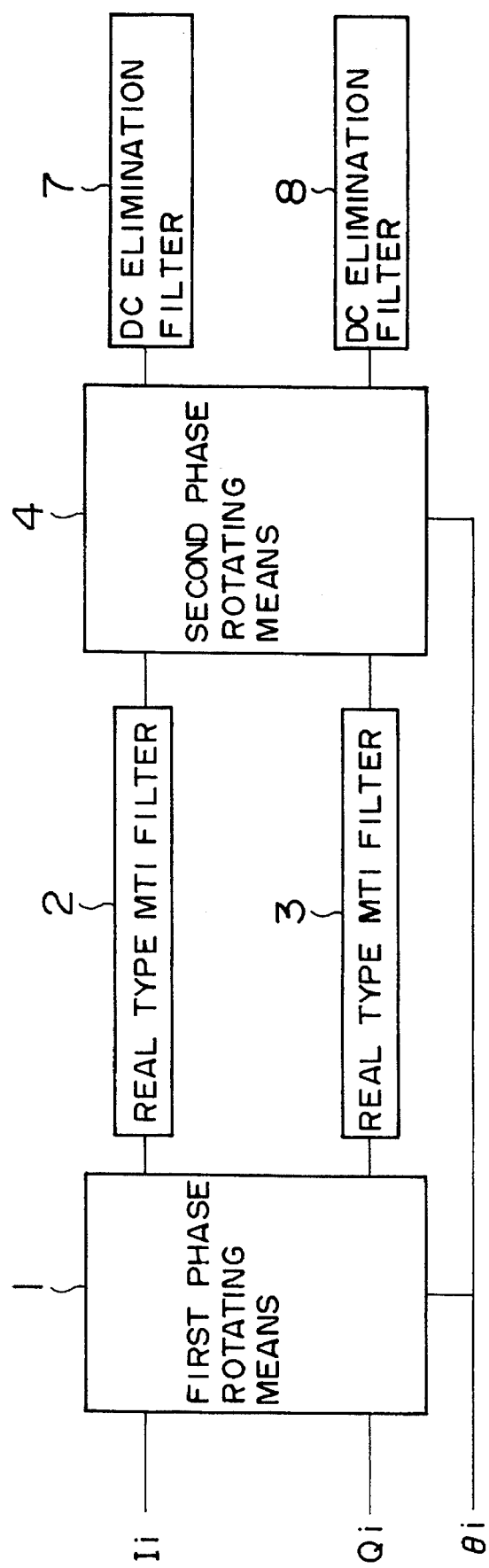
FIG. 3 is a block diagram showing the principle of another modification of the complex MTI filter according to the present invention.
Figure 4:
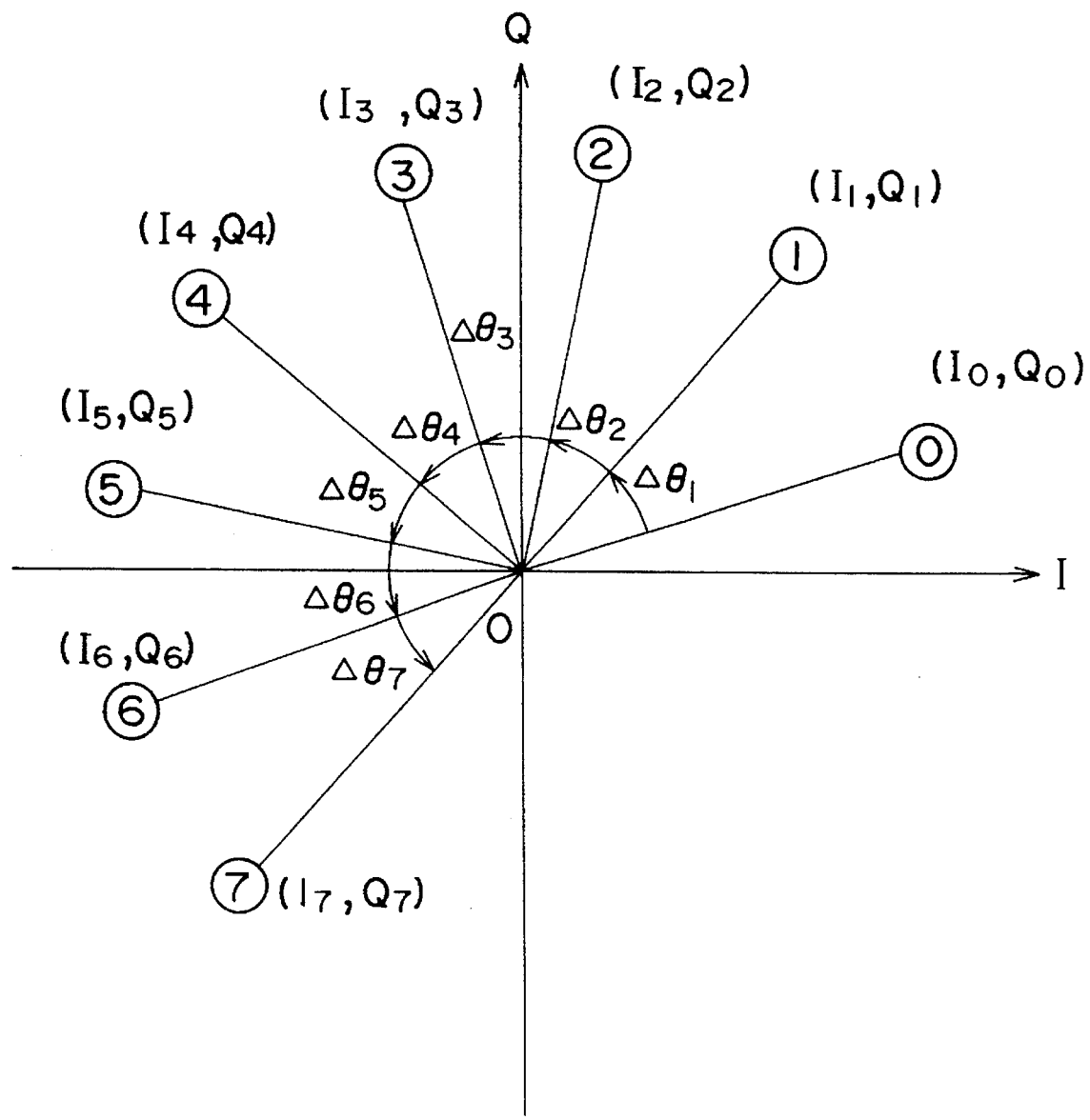
FIG. 4 is a view useful for understanding an operational principle; of the complex MTI filter according to the present invention.
Figure 5:
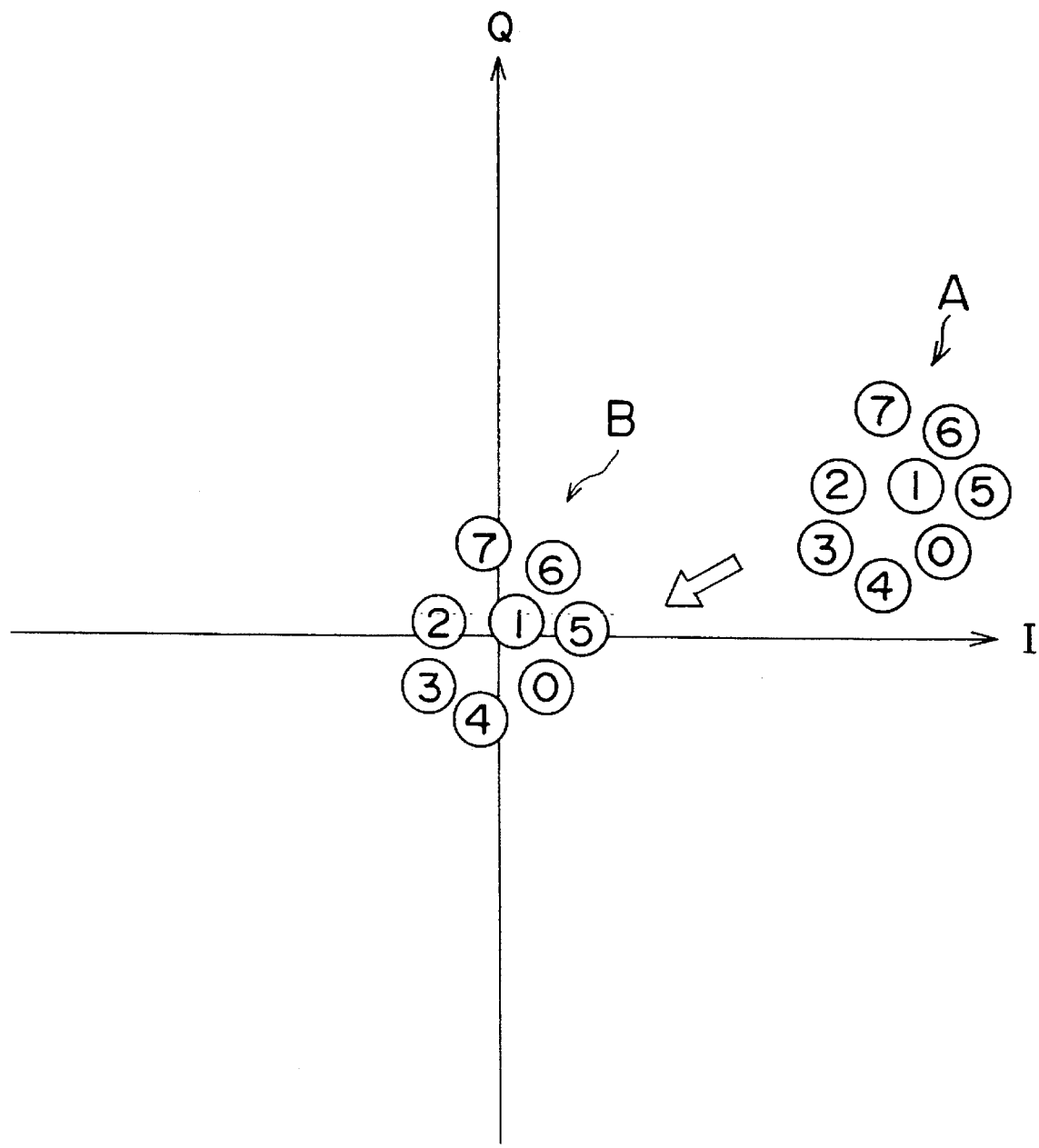
FIG. 5 is a view useful for understanding an operational principle of the complex MTI filter according to the present invention.
Figure 6:
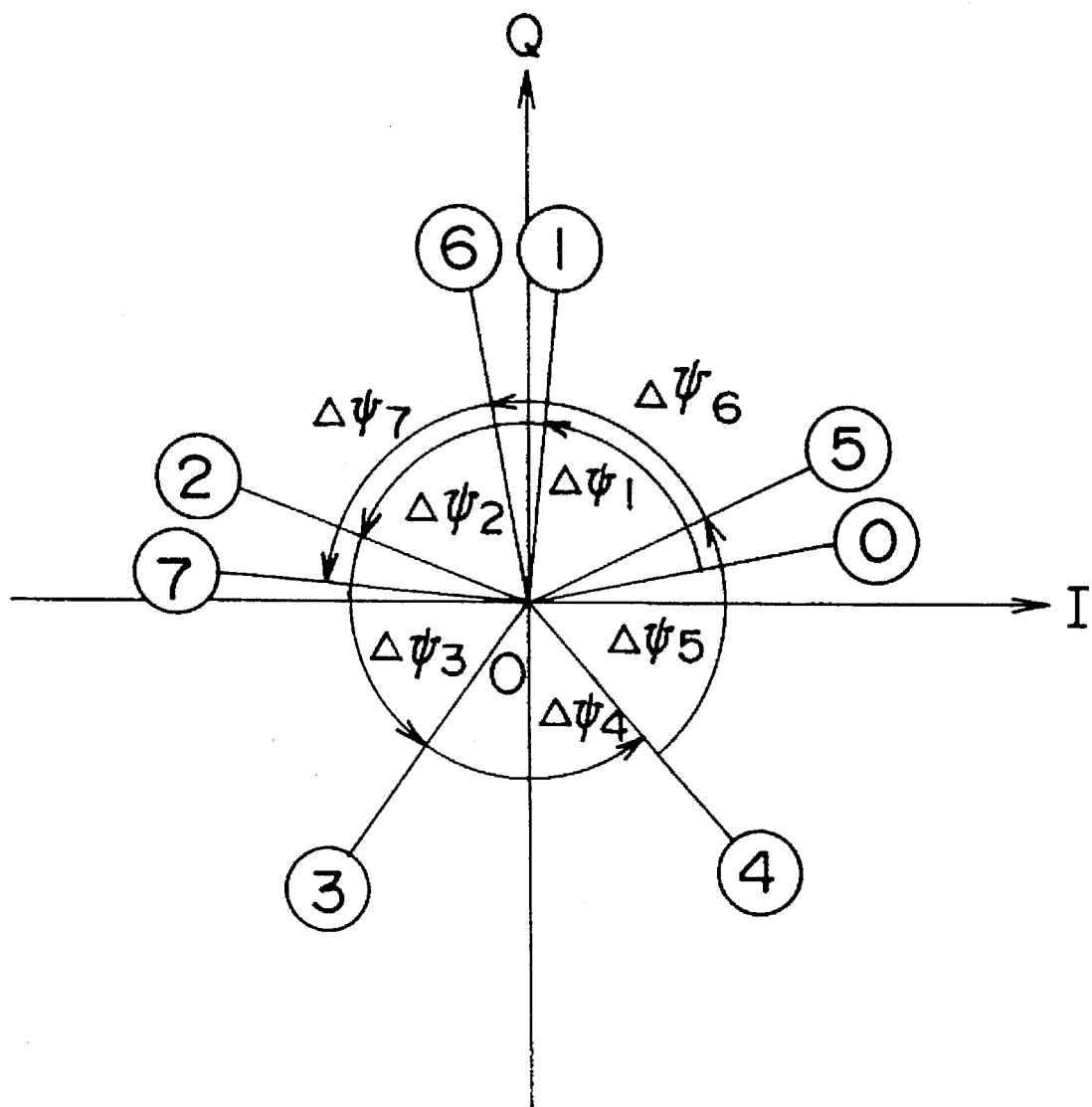
FIG. 6 is a view useful for understanding an operational principle of the complex MTI filter according to the present invention.

An angle accumulating means 100 receives an average angle $\Delta \theta$ of the phase rotation angle $\Delta \theta_i$ (i =0, 1, ..., 7) (refer to FIG. 4) due to the moving velocity of the clutter component, on each observation point within the human body under examination, while receiving eight pieces of complex data ($I_i$, $Q_i$) (i=0, 1, ..., 7) on the associated observation point. The angle accumulating means 100 calculates the accumulated angle $\theta_i$ by means of sequentially accumulating the input average angle $\Delta \theta$ itself and then passes it to a cosine and sine calculating means 200. The cosine and sine calculating means 200 is provided with a look-up table in which the angles $\theta_i$ serves as address and $\cos \theta_i$ and $\sin \theta_i$ serve as contents. In such a cosine and sine calculating means 200, when the angle $\theta_i$ is input, the $\cos \theta_i$ and $\sin \theta_i$ are obtained, and data representative of the obtained $\cos \theta_i$ and $\sin \theta_i$ are passed to a phase rotating circuit 300 and a phase reversal circuit 500.

The phase rotating circuit 300 and the phase reversal circuit 500 are the same each other in structure excepting that signs of data to be added in adders are different from each other.

Figure 8:
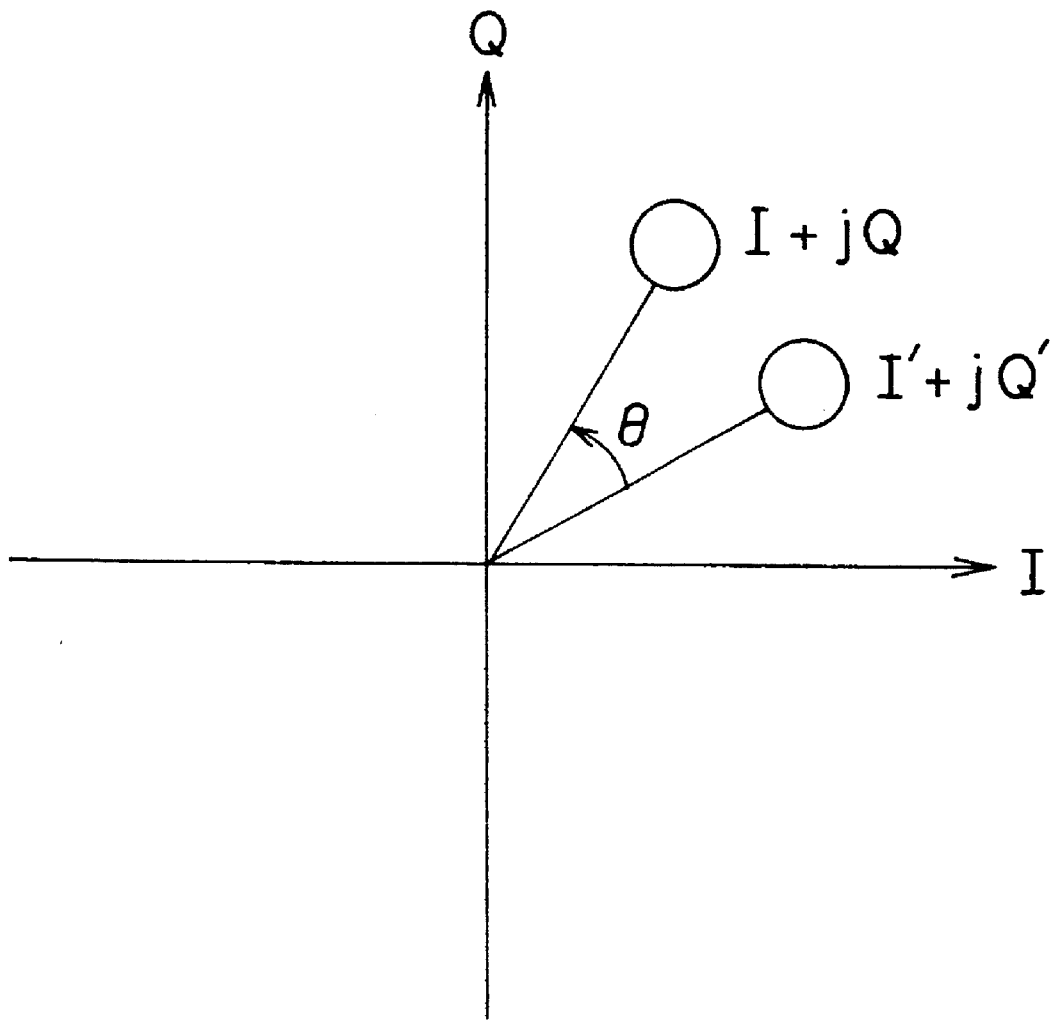
FIG. 8 is a view useful for understanding a principle of the phase rotation of a complex number.

FIG. 8 is a view useful for understanding a principle of the phase rotation of a complex number.

Assuming that a complex number I+jQ is rotated clockwise by an angle θ, and it is expressed by a complex number I'+jQ', the operation expression is given as follows:

$$\begin{aligned} I' + jQ' &= (I + jQ) \cdot \exp(-j\theta) \quad (7) \\ &= (I + jQ) \cdot (\cos\theta - j\sin\theta) \\ &= (I\cos\theta + Q\sin\theta) + j(Q\cos\theta - I\sin\theta) \end{aligned}$$

The phase reversal circuit 500 serves to rotate the input data in the opposite direction with respect to the equation (7). In this case, the operation expression is given as follows:

$$\begin{aligned} I + jQ &= (I' + jQ') \cdot \exp(j\theta) \quad (8) \\ &= (I' + jQ') \cdot (\cos\theta + j\sin\theta) \\ &= (I'\cos\theta - Q'\sin\theta) + j(Q'\cos\theta + I'\sin\theta) \end{aligned}$$

The phase rotating circuit 300 and the phase reversal circuit 500 shown in FIG. 7 perform the operation according to the equations (7) and (8), respectively.

Figure 18:
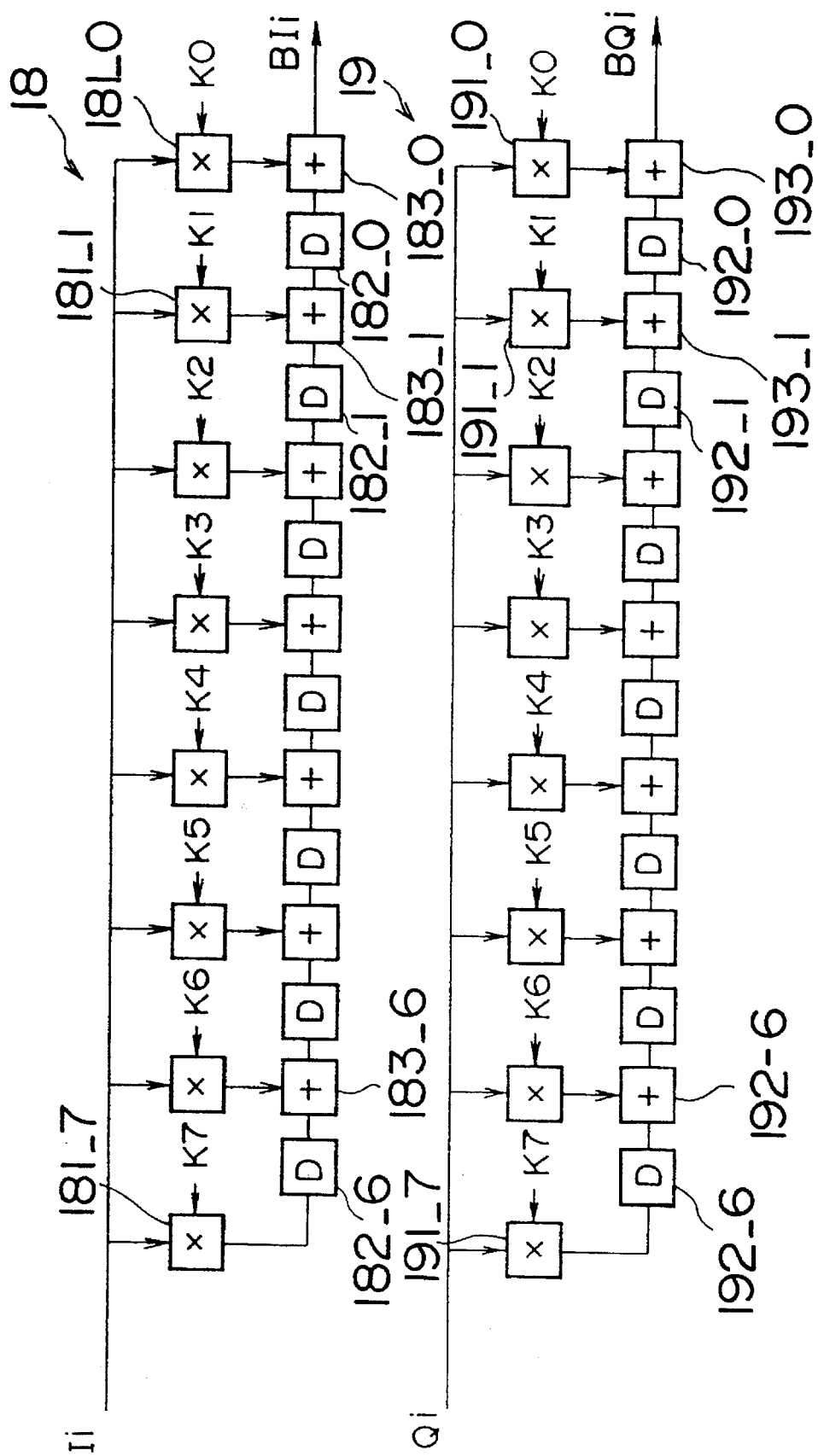
FIG. 18 is a circuit block diagram of the conventional real type MTI filter.

A real type MTI filter section 400 is provided with two pieces of eight order of moving average type MTI filters. The arrangement of those two MTI filters is the same as that of the MTI filters shown in FIG. 18, and thus the explanation thereof is omitted.

Figure 9:
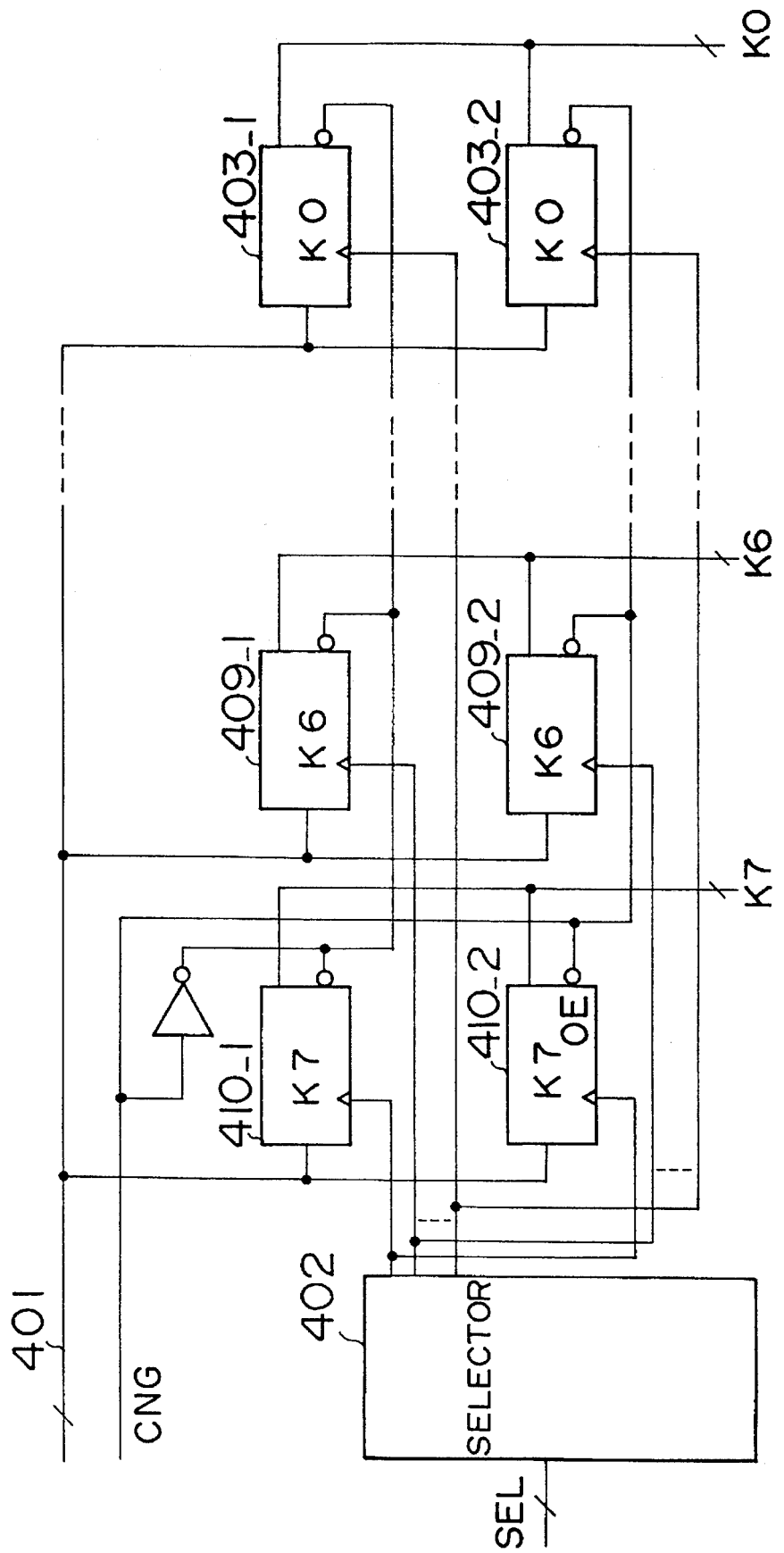
FIG. 9 is a block diagram of a factor storage circuit for storing filter factors in the complex MTI filter shown in FIG. 7.

FIG. 9 is a block diagram of a factor storage circuit for storing filter factors n the complex MTI filter shown in FIG. 7.

Figure 16:
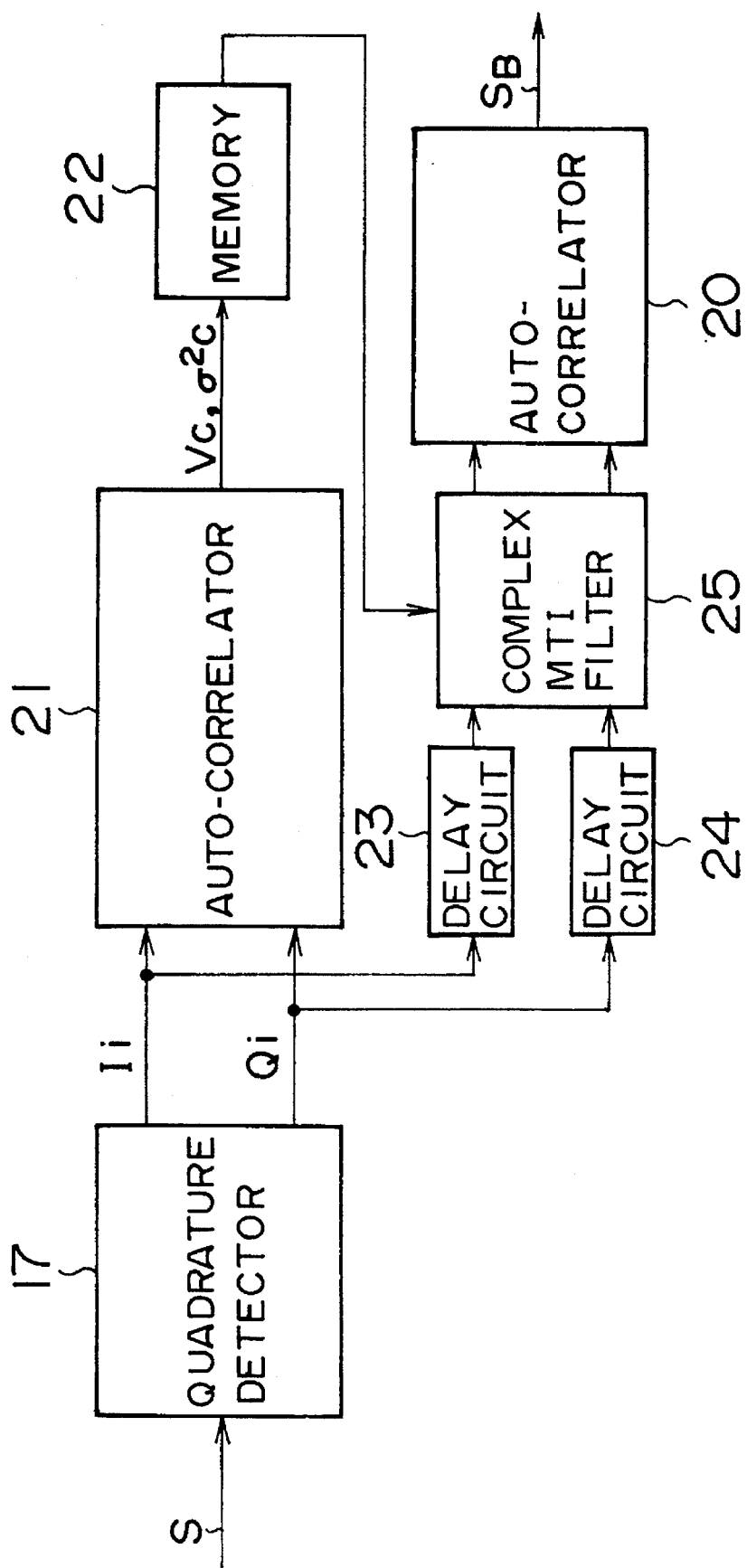
FIG. 16 is a block diagram showing a signal processing circuit corresponding to the blood flow information detecting section shown in FIG. 12.
Figure 17:
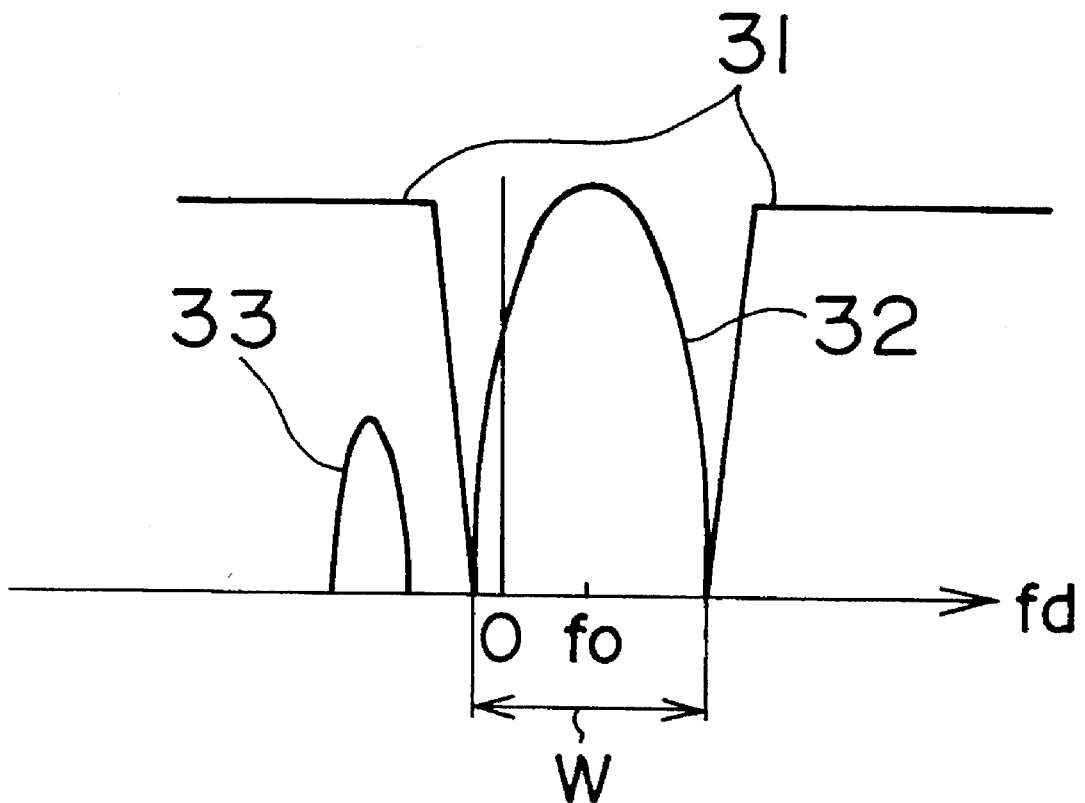
FIG. 17 is a view showing the characteristic of a complex MTI filter.

The memory 22 shown in FIG. 16 previously stores, in the form of look-up table, filter factors K0, K1, . . . , K7 to the moving velocity $V_c$ of the clutter and its variance $\sigma_c^2$. Prior to operation on each observation point within the human body under examination, the filter factors K0, K1, . . . , K7 according to the moving velocity $V_c$ of the clutter on the observation point and its variance $\sigma_c^2$ are sequentially sent out from the memory 22 in the named order onto a data line 401. In synchronism with this, a selector 402 receives a register selection signal SEL from a control circuit (not illustrated), and sequentially selects registers in accordance with the register selection signal SEL. If a switching signal CNG is of a low level "L", the registers 403_1, . . . , 409_1, 410_1 are selected, so that the filter factors K0, K1, . . . , K7 supplied sequentially through the data line 401 are set to the registers 403_1, . . . , 409_1, 410_1, respectively. The filter factors K0, K1, . . . , K7, which have been set to the registers 403_1, . . . , 409_1, 410_1, are supplied to the MTI filter shown in FIG. 7. While the MTI filter shown in FIG. 7 performs the processing on a certain observation point within the human body under examination, the switching signal CNG is inverted into a high level "H". And the filter factors K0, K1, . . . , K7 involved in the subsequent observation point are supplied through the data line 401. In synchronism with this, the selector 402 selects registers in accordance with the register selection signal SEL. Now since the switching signal CNG is of a high level "L", the registers 403_2, . . . , 409_2, 410_2 are selected, so that the filter factors K0, K1, . . . , K7 involved in the subsequent observation point are set to the registers 403_2, . . . , 409_2, 410_2, respectively. The filter factors K0, K1, . . . , K7, which have been set to the registers 403_2, . . . , 409_2, 410_2, respectively, are supplied to the MTI filter shown in FIG. 7, when the processing on the current observation point within the human body under examination is terminated, and the process goes to the processing on the subsequent observation point adjacent to the current observation point. In this manner, the registers 403_1, . . . , 409_1, 410_1 and the other group of registers 403_2, . . . , 409_2, 410_2 are alternately used, prior to the processing involved in the respective observation point in the MTI filter, to sequentially supply to the MTI filter the filter factors corresponding to the associated observation point.

Figure 10:
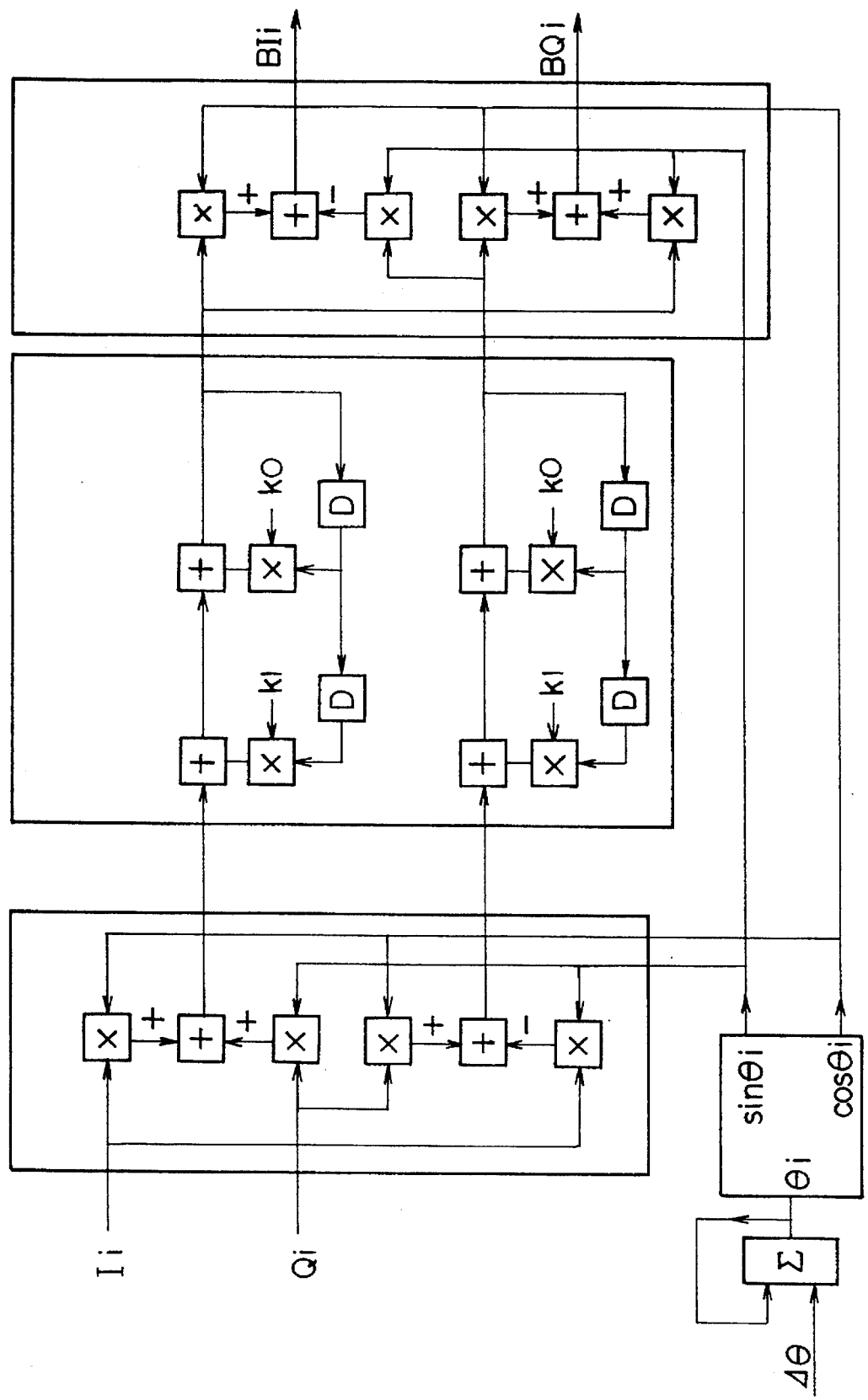
FIG. 10 is a circuit diagram of the complex MTI filter according to the second embodiment of the present invention.

FIG. 10 is a circuit diagram of the complex MTI filter according to the second embodiment of the present invention.

Figure 19:
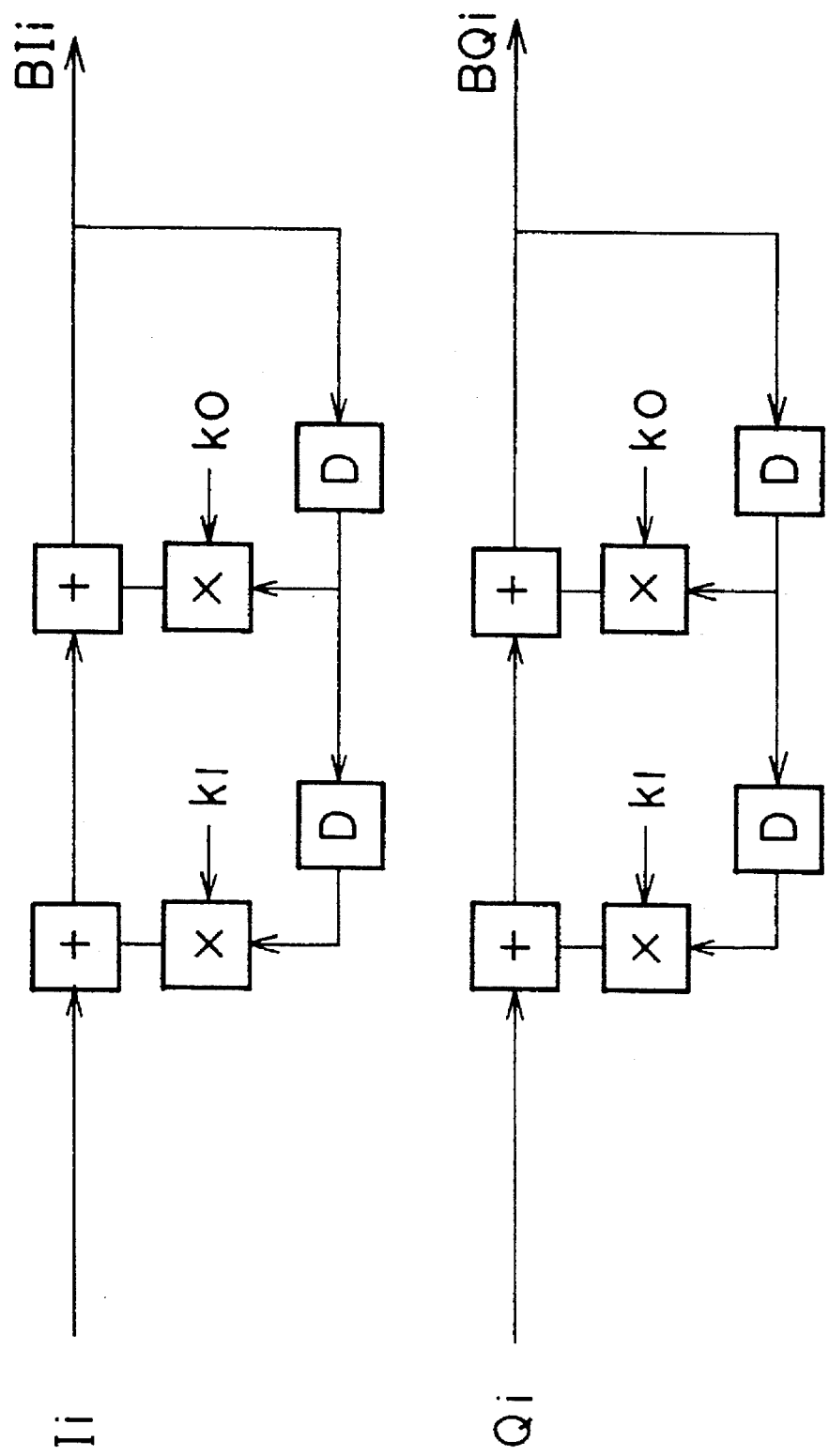
FIG. 19 is a circuit block diagram of the conventional real type MTI filter.
Figure 20:
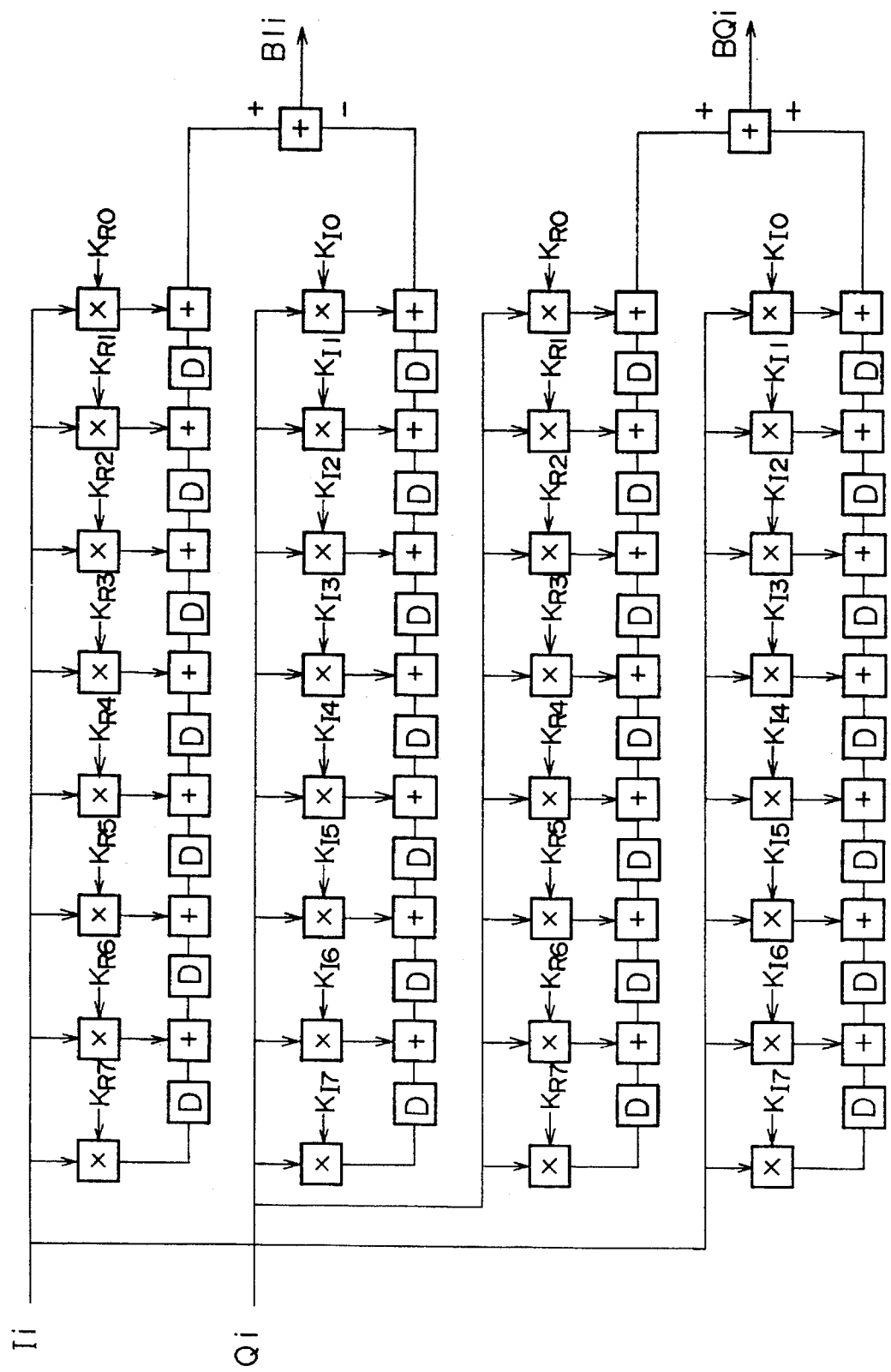
FIG. 20 is a circuit block diagram of a complex MTI filter.
Figure 21:
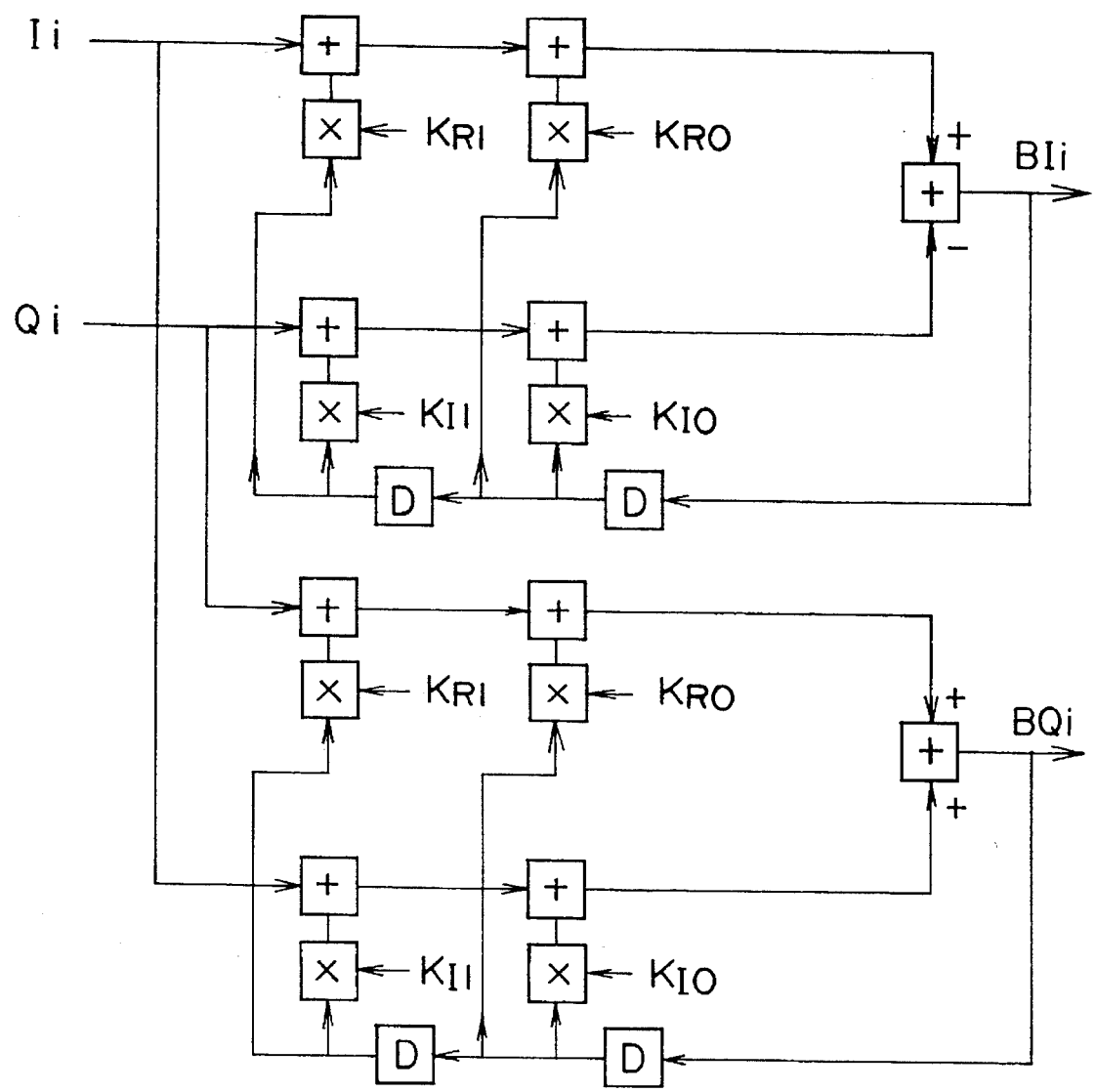
FIG. 21 is a circuit block diagram of a complex MTI filter.

The complex MTI filter according to the second embodiment is different from the complex MTI filter according to the first embodiment shown in FIG. 7 in the point that the moving average type MTI filter in the first embodiment is substituted by the autoregressive type MTI filter. This autoregressive type MTI filter is the same as that shown in FIG. 19.

Figure 11:
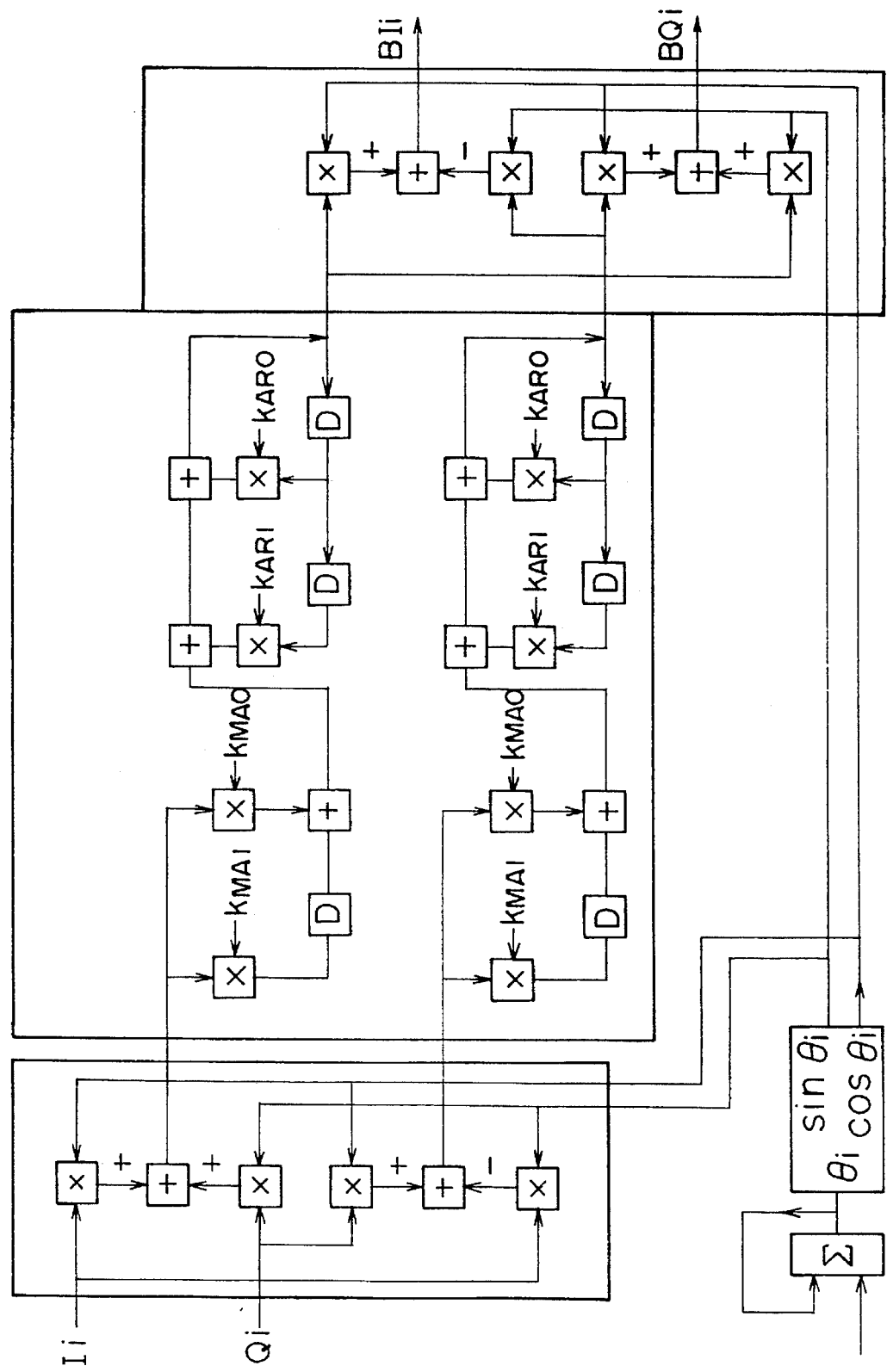
FIG. 11 is a circuit diagram of the complex MTI filter according to the third embodiment of the present invention.
Figure 12:
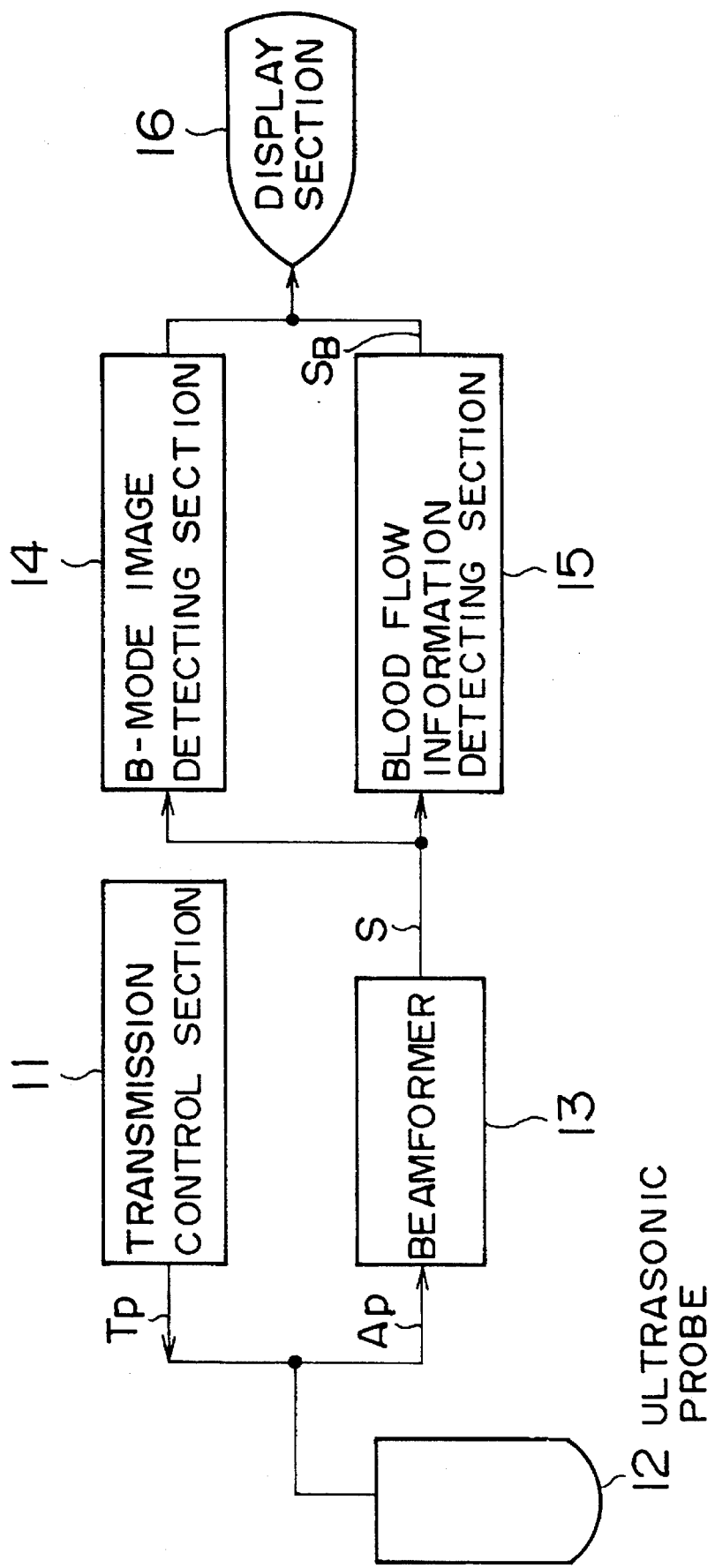
FIG. 12 is a schematic construction view of one example of a conventional ultrasonic diagnostic system.
Figure 13:
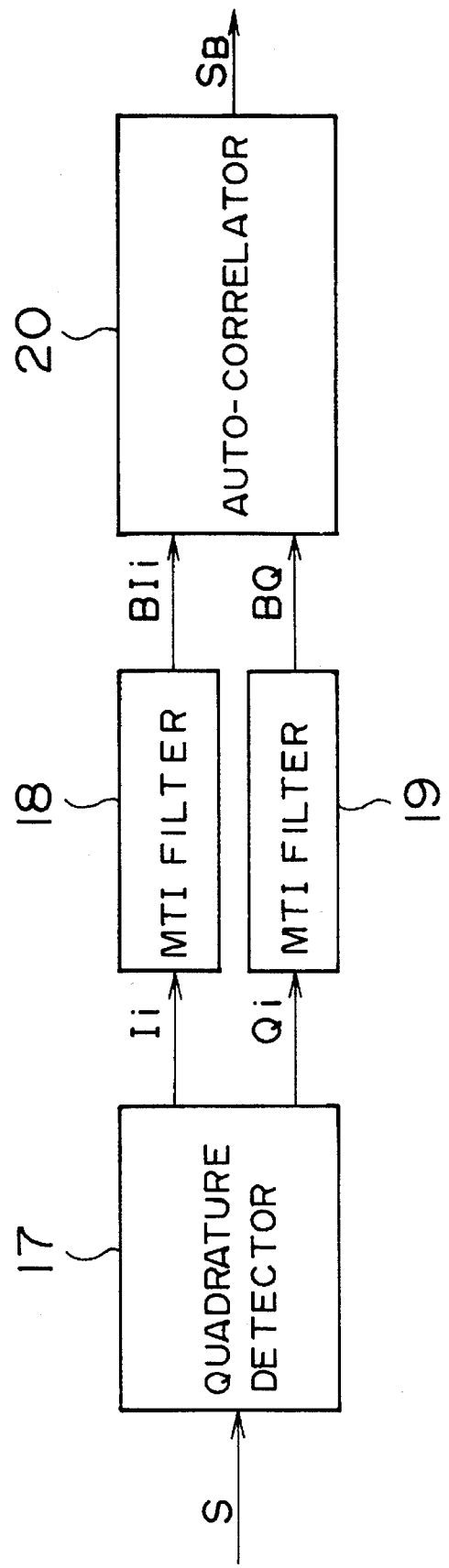
FIG. 13 is a block diagram of one example of a portion equivalent to a blood flow information detecting section 15 as shown in FIG. 12 which is involved in the conventional ultrasonic diagnostic system.
Figure 14:
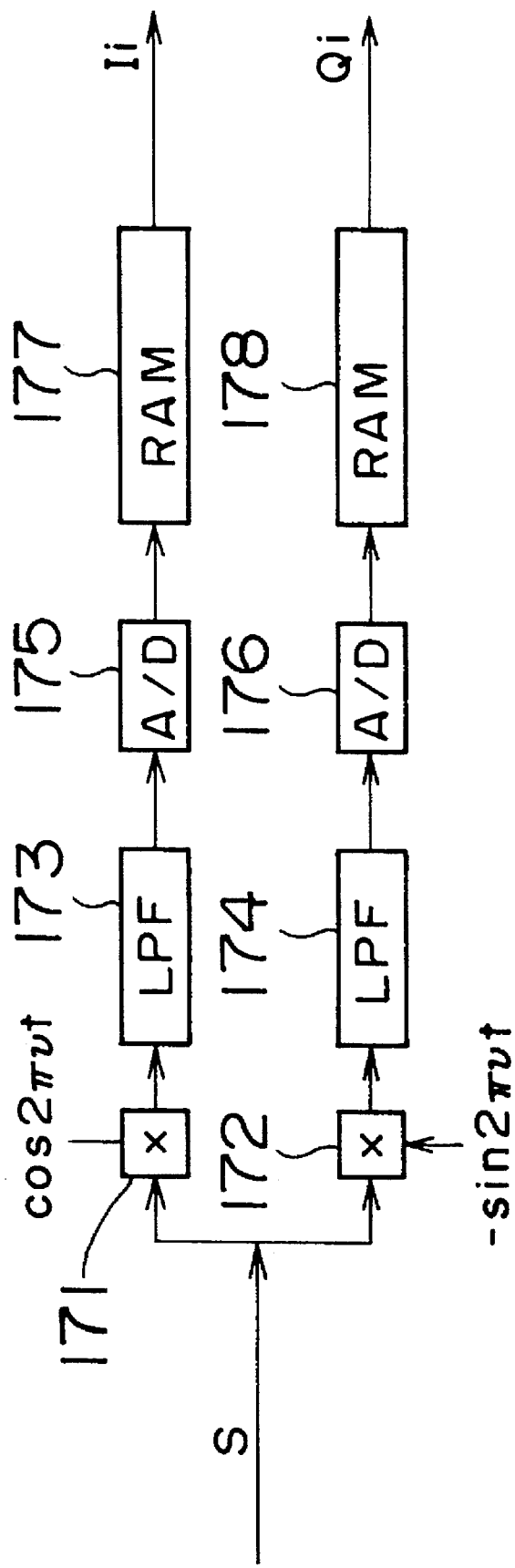
FIG. 14 is a block diagram showing an internal construction of a quadrature detector.
Figure 15A:
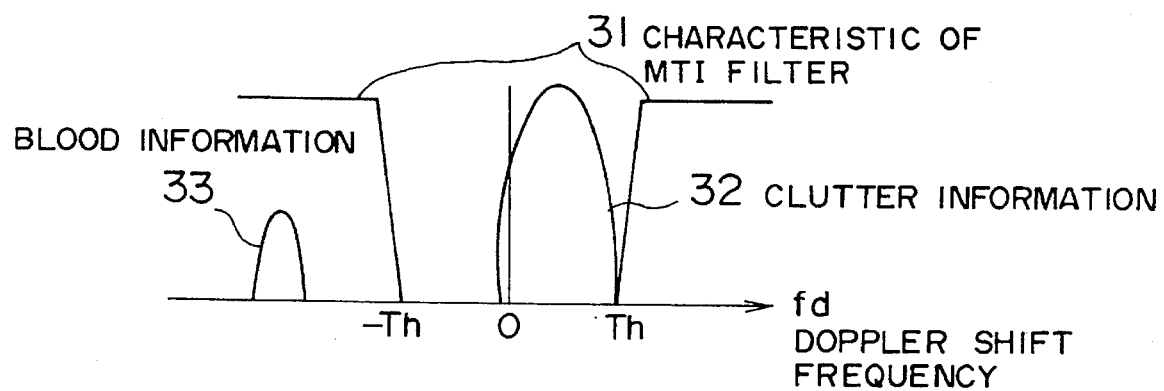
FIGS. 15(A) and 15(B) are views each showing the characteristic of the MTI filter.
Figure 15B:
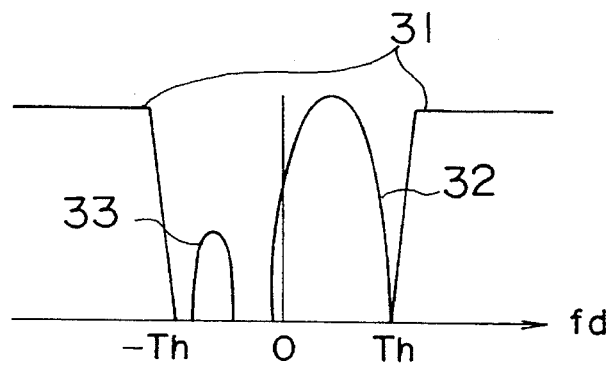

FIG. 11 is a circuit diagram of the complex MTI filter according to the third embodiment of the present invention. According to the complex MTI filter according to the third embodiment, as the real type MTI filter, there is used an MTI filter of the autoregressive moving average type which is a combination of the moving average type and the autoregressive type.

According to the complex MTI filter of the present invention, entered complex data is phase-rotated by the corresponding to the moving velocity of the clutter component. Then a predetermined filtering processing is performed by a real type MTI filter assembly, so that clutter component information is eliminated. Thereafter, the output data of the real type MTI filter assembly is reversely phase-rotated. Thus, according to the present invention, it is possible to provide a complex MTI filter which is smaller in a circuit scale and inexpensive.

The complex MTI filter of the present invention is specifically provided with the second phase rotating means 4, which is different from the technology disclosed in U.S. Pat. No. 5,170,792. Thus, in a case where the complex MTI filter of the present invention is applied to an ultrasonic diagnostic system, it is possible to detect an absoute blood flow velocity to an ultrasonic probe, but not a relative blood flow velocity to a clutter component velocity. Further, according to the present invention, it is possible to eliminate a DC component at the lower stream stage than the complex MTI filter with respect to a signal flow, thereby providing a high accuracy of ultrasonic diagnostic system.

The present invention is not limited to the particular embodiments described above. Various changes and modifications may be made within the spirit and scope of the invention.

What is claimed is:

1. An ultrasonic diagnostic system with a complex MTI filter, comprising:

probe means for detecting ultrasonic information and outputting a probe signal;

complex MTI filter means for receiving said probe signal including first phase rotating means for receiving angle data and complex data, which are associated with each other, to rotate a phase of a complex number represented by the received complex data by an angle indicated by the associated angle data;

first and second real type MTI filters for receiving data representative of the real part and the imaginary part of the complex number, which have been subjected to the phase rotation by said first phase rotating means, to provide predetermined filtering processes for said data representative of the real part and the imaginary part of the complex number, respectively;

second phase rotating means for receiving angle data and complex data of which real part and imaginary part are given with said data subjected to the predetermined filtering processes by said first and second real type MTI filters, respectively, which angle data and complex data are associated with each other, to rotate a phase of a complex number represented by the received complex data by an angle which is the same as the angle indicated by the associated angle data in the absolute value but is of inverse sign, so that an output complex data is generated; and display means for displaying information based upon the probe signal as filtered.

2. An ultrasonic diagnostic system according to claim 1, wherein said complex MTI filter means further comprises angle accumulating means for receiving angle data to sequentially accumulate angles itself indicated by said angle data so as to obtain accumulated angles, and cosine and sine calculating means for obtaining data representative of cosine and sine of said accumulated angles obtained by said angle accumulating means and supplying the thus obtained data in the form of angle data to said first and second phase rotating means.

3. An ultrasonic diagnostic system according to claim 1, wherein said first phase rotating means is provided with complex multiplication means for performing a complex multiplication of a complex number represented by the complex data entered said first phase rotating means by an additional complex number consisting of the real part and the imaginary part which are given by cosine and sine of an angle represented by the angle data entered said first phase rotating means, respectively.

4. An ultrasonic diagnostic system according to claim 1, wherein said second phase rotating means is provided with complex multiplication means for performing a complex multiplication of a complex number represented by the complex data entered said second phase rotating means by an additional complex number consisting of the real part and the imaginary part which are given by cosine and sine of an angle represented by the angle data entered said second phase rotating means, respectively.

5. An ultrasonic diagnostic system according to claim 1, wherein said complex MTI filter means further comprises factor selecting means for selecting filter factors of said first and second real type MTI filters.

6. An ultrasonic diagnostic system according to claim 1, wherein said first and second real type MTI filters each are a filter of any of moving average type, autoregressive type and autoregressive moving average type.

7. An ultrasonic diagnostic system according to claim 1, further comprising an additional filter provided after said second phase rotating means for eliminating a DC component of the complex data output from said second phase rotating means.

8. An ultrasonic diagnostic system according to claim 1, wherein said angle data is indicative of an angle corresponding to the movement of the clutter within the human body under examination, which movement being measured by utilizing an ultrasonic Doppler effect.

9. A diagnostic system with a complex MTI filter, comprising:

a beamformer for forming, based upon a probe signal, a received signal carrying ultrasonic reflection information as to each point on a scan line extending inside the subject;

a quadrature detector for practicing a quadrature detecting treatment to the received signal formed by said beamformer to generate a complex signal;

an angle arithmetic unit for evaluating angle data on the basis of the complex signal generated by said quadrature; detector;

a complex MTI filter for receiving the complex signal derived from said quadrature detector and the angle data derived from said angle arithmetic unit, including
first phase rotating means for receiving angle data and complex data, which are associated with each other, to rotate a phase of a complex number represented by the received complex data by an angle indicated by the associated angle data;

first and second real type MTI filters for receiving data representative of the real part and the imaginary part of the complex number, which have been subjected to the phase rotation by said first phase rotating means, to provide predetermined filtering processes for said data representative of the real part and the imaginary part of the complex number, respectively;

second phase rotating means for receiving angle data and complex data of which real part and imaginary part are given with said data subjected to the predetermined filtering processes by said first and second real type MTI filters, respectively, which angle data and complex data are associated with each other, to rotate a phase of a complex number represented by the received complex data by an angle which is the same as the angle indicated by the associated angle data in the absolute value but is of inverse sign, so that an output complex data is generated;

blood flow information arithmetic means for obtaining blood flow information within the subject based on the complex signal subjected to filtering in said complex MTI filter; and display means for displaying the blood flow information obtained in said blood flow information arithmetic means.

10. A diagnostic system according to claim 9, wherein said complex MTI filter means further comprises angle accumulating means for receiving angle data to sequentially accumulate angles itself indicated by said angle data so as to obtain accumulated angles, and cosine and sine calculating means for obtaining data representative of cosine and sine of said accumulated angles obtained by said angle accumulating means and supplying the thus obtained data in the form of angle data to said first and second phase rotating means.

11. A diagnostic system according to claim 9, wherein said first phase rotating means is provided with complex multiplication means for performing a complex multiplication of a complex number represented by the complex data entered said first phase rotating means by an additional complex number consisting of the real part and the imaginary part which are given by cosine and sine of an angle represented by the angle data entered said first phase rotating means, respectively.

12. A diagnostic system according to claim 9, wherein said second phase rotating means is provided with complex multiplication means for performing a complex multiplication of a complex number represented by the complex data entered said second phase rotating means by an additional complex number consisting of the real part and the imaginary part which are given by cosine and sine of an angle represented by the angle data entered said second phase rotating means, respectively.

13. A diagnostic system according to claim 9, wherein said complex MTI filter means further comprises factor selecting means for selecting filter factors of said first and second real type MTI filters.

14. A diagnostic system according to claim 9, wherein said first and second real type MTI filters each are a filter of any of moving average type, autoregressive type and autoregressive moving average type.

15. A diagnostic system according to claim 9, further comprising an additional filter provided after said second phase rotating means for eliminating a DC component of the complex data output from said second phase rotating means.

16. A diagnostic system according to claim 9, wherein said angle data is indicative of an angle corresponding to the movement of the clutter within the human body under examination, which movement being measured by utilizing an ultrasonic Doppler effect.

\* \* \* \* \*

UNITED STATES PATENT AND TRADEMARK OFFICE
CERTIFICATE OF CORRECTION

PATENT NO. : 5,483,962
DATED : January 16, 1996
INVENTOR(S) : Akira SHIBA

It is certified that error appears in the above-indentified patent and that said Letters Patent is hereby corrected as shown below:

ON THE TITLE PAGE

Item [56], in the References Cited, after "4,122,448 10/1978 Martin" insert

--... 342/162--.

Column 1, line 5, delete "1."; and line 13, delete "2.".

Column 5, line 55, change "$181_{13}0$" to --181__0--.

Column 10, line 28, delete "$\zeta$" and insert --$\theta$--.

Signed and Sealed this

Fourteenth Day of May, 1996

Attest:

BRUCE LEHMAN

*Attesting Officer*    *Commissioner of Patents and Trademarks*